(12) United States Patent
Cassingham et al.

(10) Patent No.: US 10,987,093 B2
(45) Date of Patent: Apr. 27, 2021

(54) METHOD AND APPARATUS FOR WOUND SEALANT APPLICATION

(75) Inventors: Charles Vaughn Cassingham, Newport Beach, CA (US); William Jerome Mezger, Trabuco Canyon, CA (US)

(73) Assignee: NeoMend, Inc., Irvine, CA (US)

( * ) Notice: Subject to any disclaimer, the term of this patent is extended or adjusted under 35 U.S.C. 154(b) by 0 days.

(21) Appl. No.: 13/080,223

(22) Filed: Apr. 5, 2011

(65) Prior Publication Data

US 2011/0245866 A1  Oct. 6, 2011

Related U.S. Application Data

(60) Provisional application No. 61/320,877, filed on Apr. 5, 2010.

(51) Int. Cl.
*A61B 17/00* (2006.01)

(52) U.S. Cl.
CPC ............ *A61B 17/00491* (2013.01); *A61B 2017/00495* (2013.01); *A61B 2017/00544* (2013.01); *A61B 2017/00548* (2013.01)

(58) Field of Classification Search
CPC ........ A61B 17/00491; A61B 17/00495; A61B 17/00522; A61B 2017/00495;
(Continued)

(56) References Cited

U.S. PATENT DOCUMENTS

| 4,067,479 A | * | 1/1978 | Moline ............... B01F 7/086 222/94 |
| 4,735,616 A | | 4/1988 | Eibl et al. |

(Continued)

FOREIGN PATENT DOCUMENTS

| JP | S61-293443 A | 12/1986 |
| JP | 6-52839 U | 7/1994 |

(Continued)

OTHER PUBLICATIONS

Japanese Patent Application No. 2013-503838 Office Action dated Jan. 6, 2015.
(Continued)

*Primary Examiner* — Benjamin J Klein
(74) *Attorney, Agent, or Firm* — Wolf, Greenfield & Sacks, P.C.

(57) ABSTRACT

Devices and methods are disclosed for delivering sealing compound to a wound in animals, including humans. Such wound sealing is important after deep skin penetrating lacerations or subsequent to internal wounds. The apparatus utilize an aerosol dispensing system that both mixes and applies a multi-part sealant compound. The aerosol system includes a plurality of sealant component chambers, a source of pressurized gas, an aerosol mixing head, a pressure regulator, a pneumatic switch, and a component pumping mechanism. The aerosol system, either a reusable or a disposable device, is further provided with a system that keeps dry components from liquid components and then automatically mixes the liquid and dry components prior to application. The system provides for easy control over the application, inexpensive manufacture, and simplified preparation, thus minimizing the time needed for application and enhancing the potential outcomes of the patient.

18 Claims, 12 Drawing Sheets

(58) Field of Classification Search
CPC .......... A61B 2017/00544; A61B 2017/00548; B05B 7/0408; B05B 7/062; B05B 7/24; B05B 7/2445; B05B 7/2489–2497; B05B 11/0037–0056; B05B 11/02; B05B 11/025; B05C 17/00553; B05C 17/00573; B05C 17/015; B29B 7/7452
See application file for complete search history.

(56) References Cited

U.S. PATENT DOCUMENTS

| | | | | |
|---|---|---|---|---|
| 5,064,098 | A * | 11/1991 | Hutter, III | B05C 17/00553 222/137 |
| 5,582,596 | A * | 12/1996 | Fukunaga | A61B 17/00491 222/137 |
| 5,816,445 | A * | 10/1998 | Gardos | B01F 15/0454 222/1 |
| 6,371,975 | B2 | 4/2002 | Cruise et al. | |
| 6,458,147 | B1 | 10/2002 | Cruise et al. | |
| 6,461,361 | B1 | 10/2002 | Epstein | |
| 6,464,663 | B1 * | 10/2002 | Zinger | A61B 17/00491 222/390 |
| 6,527,749 | B1 * | 3/2003 | Roby et al. | 604/191 |
| 6,562,059 | B2 | 5/2003 | Edwards et al. | |
| 6,565,539 | B1 * | 5/2003 | Zinger | A61B 17/00491 604/191 |
| 6,733,515 | B1 | 5/2004 | Edwards et al. | |
| 6,743,248 | B2 | 6/2004 | Edwards et al. | |
| 6,783,514 | B2 | 8/2004 | Tovey et al. | |
| 6,830,756 | B2 | 12/2004 | Hnojewyj | |
| 7,217,254 | B2 * | 5/2007 | Kirwan | A61B 17/00491 604/191 |
| 7,537,174 | B2 * | 5/2009 | Redl et al. | 239/321 |
| 7,699,803 | B2 * | 4/2010 | Nayak | A61M 5/19 604/72 |
| D791,275 | S * | 7/2017 | Muller | D23/208 |
| 9,731,258 | B2 * | 8/2017 | Janssen | B05C 17/00566 |
| 2001/0011162 | A1 | 8/2001 | Epstein | |
| 2002/0165483 | A1 | 11/2002 | Miller et al. | |
| 2003/0136859 | A1 * | 7/2003 | Borden | B05C 17/00516 239/1 |
| 2005/0281883 | A1 * | 12/2005 | Daniloff et al. | 424/489 |
| 2007/0191781 | A1 * | 8/2007 | Richards | A61B 17/00491 604/191 |
| 2007/0225645 | A1 * | 9/2007 | Tarinelli | A61M 35/003 604/131 |
| 2008/0103564 | A1 | 5/2008 | Burkinshaw et al. | |
| 2008/0144426 | A1 * | 6/2008 | Janssen | B01F 7/00291 366/130 |
| 2009/0005731 | A1 * | 1/2009 | Yokoyama | A61B 17/00491 604/83 |
| 2009/0152305 | A1 | 6/2009 | Redl et al. | |
| 2009/0209916 | A1 | 8/2009 | Peindl et al. | |

FOREIGN PATENT DOCUMENTS

| | | |
|---|---|---|
| JP | 2002-513654 A | 9/2001 |
| JP | 2002-513654 A | 5/2002 |
| JP | 2008-505709 A | 2/2008 |
| JP | 2008-526436 A | 7/2008 |
| JP | 2009-531142 A | 9/2009 |
| WO | WO 95/31138 A1 | 11/1995 |
| WO | 1998/010703 A1 | 3/1998 |
| WO | WO 2006/014568 A2 | 2/2006 |
| WO | 2006-076427 A2 | 7/2006 |
| WO | WO 2007/126845 A2 | 11/2007 |

OTHER PUBLICATIONS

Office Action dated Jan. 6, 2015 for Japan Application 2013-503838.
Supplementary European Search Report and Written Opinion for EP11766590 dated Nov. 29, 2016.

* cited by examiner

METHOD AND APPARATUS FOR WOUND SEALANT APPLICATION

CROSS-REFERENCE TO RELATED APPLICATIONS

This application claims benefit to and priority of U.S. Provisional Patent Application No. 61/320,877 filed on Apr. 5, 2010 entitled "Method and Apparatus For Wound Sealant Application," the entire contents of which are hereby incorporated by reference.

FIELD OF THE INVENTION

The present invention relates to methods and devices for sealing wounds, either open or closed, wherein a section of tissue is damaged and undergoing hemorrhage, following either trauma or surgery. More specifically, the present invention relates to devices for providing multi-component sealants to a wound.

BACKGROUND OF THE INVENTION

Following various types of surgery, it is beneficial to seal off a wound. While suture placement is often the preferred approach, the use of sealants is becoming an increasingly important adjunct to a surgeon's armamentarium. Typical surgical applications of sealants include dural repair, in either the brain or spinal cord, fixation of a polymer mesh within a hernia repair, and sealing a damaged lung or spleen. Dural repair is especially useful in closing a laminectomy or microlaminectomy of the spinal cord. Certain sealants also are finding use in repairing a pericardial incision following cardiac surgery as well as in pelvic or abdominal surgery. Other applications include prevention of surgical adhesions, tissue augmentation, tissue bulking, and drug delivery. Such sealants are also finding application in hemorrhage control following traumatic wounds to the body.

Closure of a deep laceration or wound has traditionally been performed by manually applying pressure to the vessel adjacent the main artery feeding the wound site, if possible. This procedure requires the continuous attention of at least one medical staff member to apply pressure to the vessel puncture site and can take 30 minutes or longer. Of course, an internal wound may be difficult or impossible to seal by application of external pressure. With a weeping wound, such as can occur with exposure of a large tissue plane, it is difficult or impossible to prevent hemorrhage by applying pressure to a specific artery.

One possible way of applying wound sealant is by way of aerosol or spray dispensing. The prior art systems for application of wound sealants require the user to withdraw a bolus of liquid from a sealed container and transfer that liquid to a second container where it is mixed with a dry component. The mixed wet and dry components are then separately affixed to a delivery syringe assembly which is then mated to mixing heads, aerosol generators, hand-grips and the like. The prior art systems are very cumbersome and/or require attachment to an external source of pressurized gas by way of a gas line.

Likewise, the individual components must be mixed and applied before hardening within the delivery system, which has also been a concern with previous delivery systems. Current prior art systems tend to clog after they have been used, which makes the system inoperable until the system has been cleaned and the clog has been removed. Despite the various devices that have been developed for delivering sealing compounds to wounds, the need continues for a simpler system to apply multi-part sealing compounds wherein the system requires less setup time prior to use.

SUMMARY OF THE INVENTIONS

The present invention relates to a device, or apparatus, for introducing a sealing compound, which can be a biostable or resorbable hydrogel, into a wound using aerosol mixing. The invention more specifically relate to apparatus and methods for mixing and delivering multi-part sealing compounds to wounds or tissue surfaces, both skin-penetrating and internal wounds without skin penetrations. The present invention encompasses wound closure sealant applicators that deliver a two-part, or multi-part, sealing material to the wound to create wound closure, tissue coatings, and/or hemostasis. The applicators are adapted to be used through an externally communicating wound, or with an internal wound by way of laparoscopic access. Other applications for the device include delivery of materials for the purpose of localized drug delivery, to provide bulking or tissue augmentation, and to provide a barrier for the prevention of surgical adhesions.

U.S. Pat. Nos. 6,371,975, 6,458,147, 6,562,059, 6,733,515, and 6,743,248, 6,830,756, the entirety of which are hereby included herein by reference, disclose systems to introduce biological repair materials, including compounds comprising the components albumin and polyethylene glycol (PEG) into the area surrounding and exterior to a vessel penetration site, the combination of said materials creating an adhesive sealing matrix. A primary use of these systems is in the closure of vessel puncture, although the sealant material used therein creates an excellent wound seal, dural seal, adhesion barrier, and the like.

A primary aspect of the inventions is portability. In a preferred embodiment, the device is internally powered and requires no external electrical or gas pressure sources. The device can use either an internal battery or an internal source of pressurized gas.

Alternatively, the device can be powered by external sources of electricity or gas, with the external source of gas or electricity delivered to the device by a high-pressure gas line, an electrical cable, or both. The power source further includes an adjustment mechanism such as a pressure regulator for the gas source or a level control for the electrical source. The adjustment mechanism can be pre-set and further be non-adjustable by the user, or it can comprise a knob, lever, multi-position switch, or other adjustment control that is operable by the user.

Another aspect of the inventions is the prevention of clogging of the outlet ports of the spray tip by the sealing compound. Sealing compounds that require mixing generally solidify quickly after mixing. A multi-part compound is created by mixing two or more components that are separately delivered from individual reservoirs to another specified mixing area. The addition of one or more high-pressure turbulent gas jets provides the necessary mixing to ensure that the sealing compound is fully functional as a sealant.

The individual component containing reservoirs may be arranged in various ways. In one example, the outlet port for one of the components, albumin for example, is positioned behind the outlet port of another compound, for example polyethylene glycol (PEG), so that mixed material cannot splash retrograde into the albumin channel and create a blockage or stenosis. In an alternative arrangement, the components are mixed within a chamber or tube while maintained at a pH level where gelling is retarded. The mixed components are then buffered to a pH that promotes rapid gelling just at the outlet of the system. At neutral pH, the sealing compound becomes adherent and could cause blockage of delivery channels. For this reason, the buffering is performed just at the exit from the delivery channels. In a further arrangement, the component flow channels are automatically cleared by fluid, either air, water, a buffered solution, or other fluid, which is forced through the flow channels and spray head following each application.

Another aspect of the inventions is improved simplicity of component mixing. As previously stated, the mixed components may comprise human albumin and polyethylene glycol (PEG). The albumin is generally storable and transportable as a liquid, or solution, in its final state. For purposes of extended shelf life, however, the polyethylene glycol solution is generally fabricated using water ($H_2O$) and dry polyethylene glycol (PEG), which are kept separate until just before use. The mixing of the water solvent and PEG cross-linking agent, by the user, is a cumbersome and time-consuming activity. The albumin solution may be packaged within a first syringe, while the PEG and water are packaged within a second syringe, but separated by a vapor-proof barrier. An initial loading function comprises pressurizing the syringe with the water so that the separation barrier moves to a syringe location further comprising a shunt through which the water, under pressure can be injected into the dry PEG powder. The PEG cross-linking agent and water, or solvent, are fully mixed by manual shaking, or by agitation generated by the pressurized water jets.

The PEG may also be stored in one syringe as a powder and the water is stored in a separate syringe. Initialization of the system involves withdrawing water from its syringe into the PEG syringe, again with jet or agitation mixing. Forward pressure on the PEG/water solution simultaneous with forward pressure on the albumin solution causes these two final components to be advanced into a mixing apparatus for application to the patient.

Another aspect of the inventions is the sterility and disposability of the device and system. The entire device may be provided in sterile packaging, in aseptic packaging. Once usage is completed, the entire device is disposed of, or is discarded. Alternatively, the syringe system may be provided as a sterile and/or disposable device, while the applicator is reusable. In another embodiment, the reusable applicator is reusable but is sterilizable and cleanable. Sterilization is carried out using gamma irradiation, electron beam irradiation, steam sterilization (autoclaving), ethylene oxide sterilization, or the like.

Another aspect of the invention relates to the method of use. The sterile components of the assembly are withdrawn from its sterile packaging. It is assembled to a reusable applicator. The power source is inserted into the applicator and checked to ensure a full charge. A lock is released, pre-loading the syringes and making sure any necessary mixing is completed. Next, the device is aimed at the wound area to be sealed. A trigger is actuated, projecting the sealing compound out the front of the system toward the target tissue along with a gas jet for the purpose of mixing, aerosolizing, and delivery. The spray pattern is preferably pre-determined and well defined, generally taking on the shape of a solid cone, a fan, or other pre-determined pattern. An interlock may be used that permits only a specified amount of the sealing compound, 2-cc for example, to be applied to the wound. Defeating, unlocking, or repositioning the interlock allows a second 2-cc bolus of sealing compound to be applied to the wound. Follow-on applications can be applied as required. Defeating the interlock can be done by a separate maneuver or simply by releasing and then re-squeezing the trigger mechanism.

The current invention may include an apparatus for delivery of the sealing compound, or adhesion barrier, to internal wounds. A laparoscopic sheath or trocar is attached to the delivery end of the device. The apparatus is configured with a long distal end, approximately 10 to 30 cm long. The long distal end comprises a plurality of separate delivery channels for the sealing compound components as well as a lumen or channel for delivery of the aerosolizing high-pressure gas.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention.

DETAILED DESCRIPTION OF THE INVENTIONS

Figure 1:
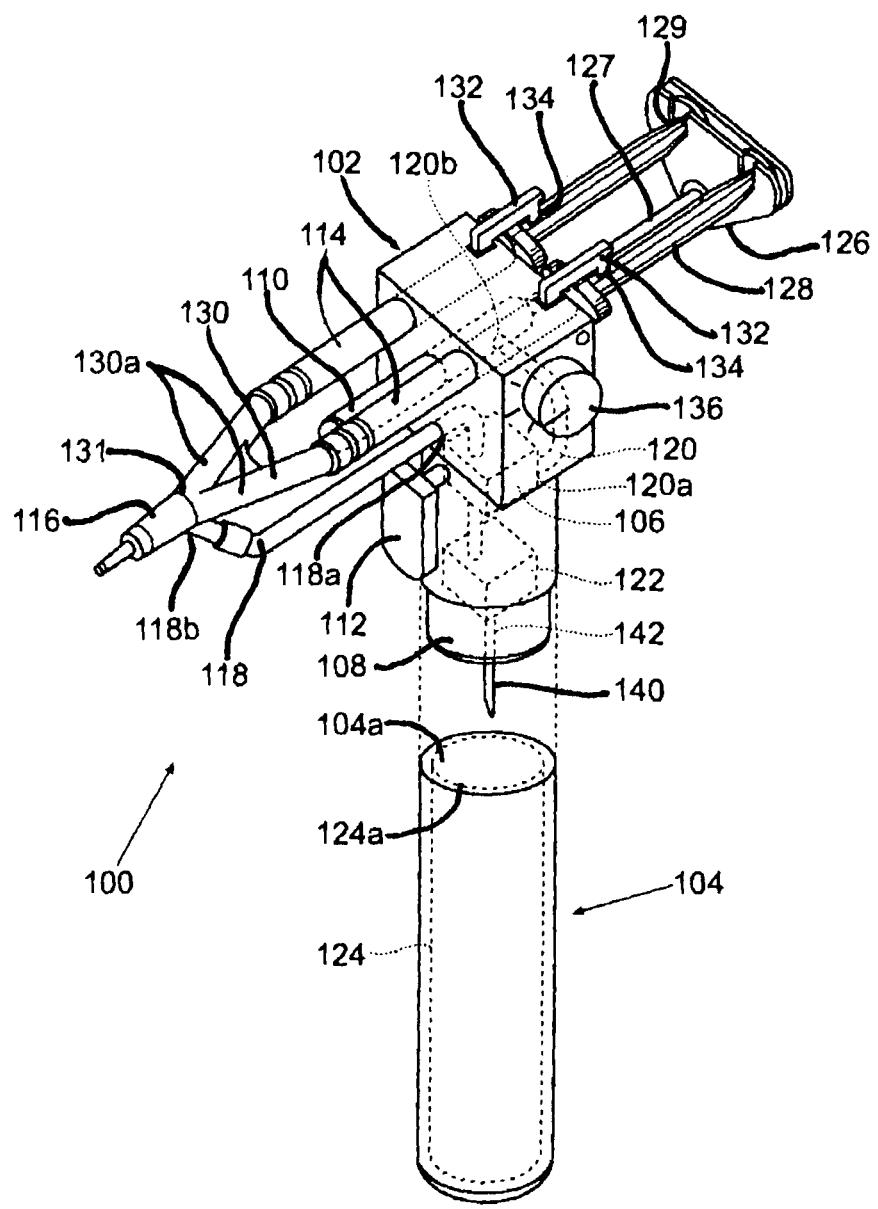
FIG. 1 illustrates a prospective view of an aerosol applicator comprising a gas source and a dual syringe reservoir, according to an embodiment of the invention.

In accordance with one or more embodiments of the inventions, a wound sealing apparatus and method, are described herein. In order to fully specify this preferred design, specific details of various embodiment are set forth, such as the composition of the sealing material and apparatus for connecting the sealing catheter to already placed introduction sheaths. It should be understood, however that these details are provided only to illustrate the presented embodiments, and are not intended to limit the scope of the present invention.

Gelling properties of biomedical sealants, fabricated from components such as polyethylene glycol in aqueous solution and human albumin, are dependent on a number of factors. Optimal gelling of the sealant solution can be achieved without the use of a static mixer if, during spraying, both fluids are dispersed into small droplets and a uniform, combined spray of both fluids is achieved. A type of mixing and spraying, known as aerosol spraying, produces very fine droplet size and good mixing, but requires that airflow and fluid dispensing rates be within optimal ranges. Aerosol spraying of a two- or multi-component sealant can achieve both component mixing and spray application to the target tissue. When sealant-dispensing rates are too high for a given gas flow rate, a fluid stream, rather than a spray, can result with inadequate mixing, incomplete gelling, and poor material coverage. The sealant components can be adjusted to mix at a specified ratio, with a possible ratio being a ratio of 1:1 by volume. Using a commercial mixing head, it has been determined that preferred flow rates include 12.5 liters per minute for the gas and 2.4 cc/sec for the sealant, 11.4 liters per minute for the gas and 2 cc/sec for the sealant, and 10.0 liters per minute for the gas and 1.3 cc/sec for the sealant. The gas pressures corresponding to given gas flow rates can be adjusted as follows: 20 PSI for 12.5 liters/min, 18 PSI for 11.4 liters/min, 15 PSI for 10 liters/min, and 13 PSI for 8.5 liters per minute. Acceptable mixing occurs with gas flow rates of 11.4 l/min and 2.4 cc/sec for the sealant, 10.0 liters/min for the gas and 1.6 to 1.8 cc/sec for the sealant, and 8.5 liters/min for the gas and 1.3 cc/sec for the sealant. With slower sealant delivery rates, for example, ½ cc per second, aerosol gas pressures of 12 to 15 PSI provide acceptable spray coverage. Parametrically, a preferred relationship between the gas flow rate (X liters/min) and the sealant flow rate (Y cc/sec) can be approximated as $Y(cc/sec)=0.44*X(l/min)-3.10$, while an acceptable relationship is approximately $Y(cc/sec)=0.39*X(l/min)-2.15$. Provided the flow rates allow for proper sealing without clogging the device, the rates will fall within the scope of the present invention.

Generally describing the present invention, the proximal end of the instrument refers to the delivery end of the instrument, and the distal end is the opposing end. A lumen may be described as an axially elongate channel within a catheter, tube or instrument. The lumen may exit the instrument at the proximal or distal end, or both, or it may be sealed to prevent the outflow or inflow of material.

Figure 4:
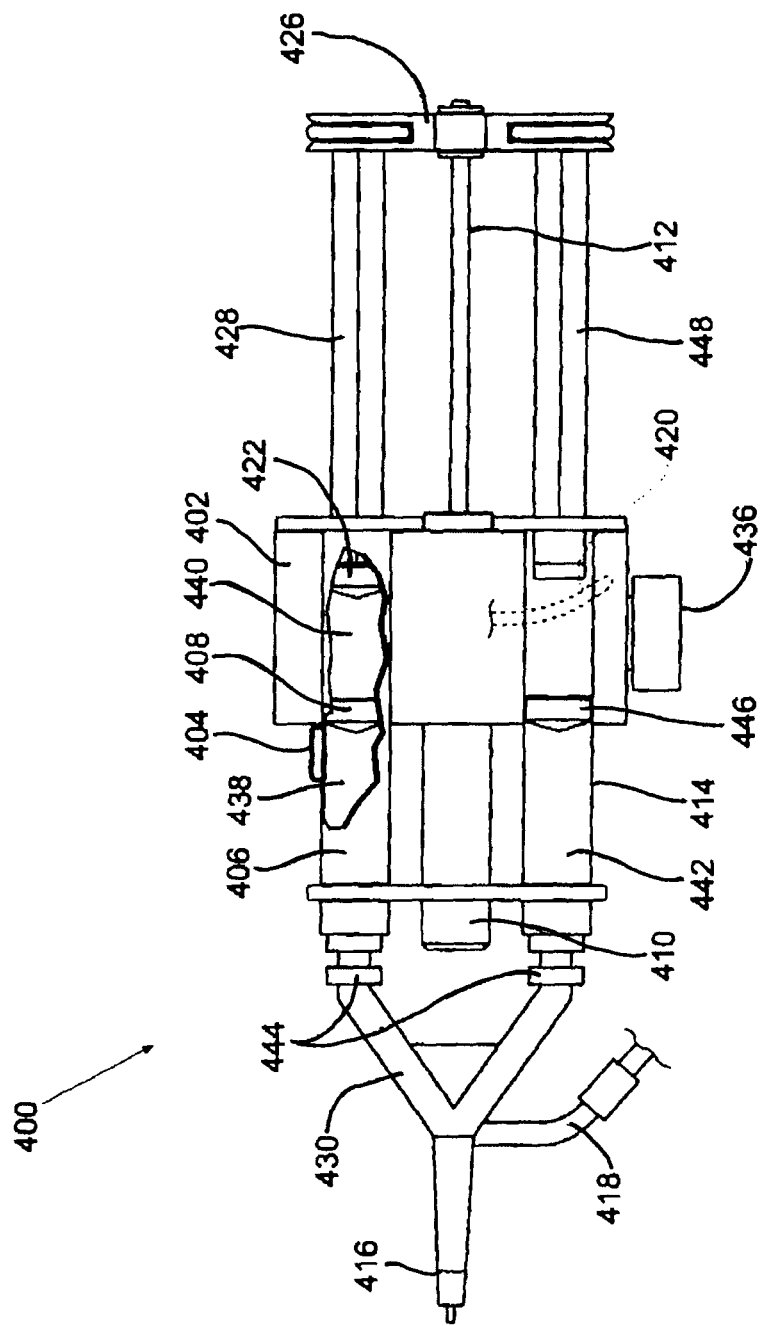
FIG. 4 illustrates a top, partially cut-away view of an aerosol dispenser comprising a lyophilizing or single syringe mixing system, according to an embodiment of the invention.

FIG. 1 illustrates a perspective view of a self-contained, pneumatically powered aerosol dispenser system 100. The system 100 is an exemplary overview of the invention as a whole, and it should be understood that the features shown and described with respect to FIG. 1 could be incorporated with the features of the other figures where appropriate.

The pneumatic aerosol dispensing system 100 generally comprises a main housing 102 and a handle 104. The housing 102 contains a pneumatic cylinder pressure regulator 106 (shown in phantom). The housing is affixed to a puncture head 108, which allows the handle 104 to be attached to the housing 102, preferably in a threaded or screw-like fashion. When removed from the puncture head 108, the handle 104 has an open top **104*a* that accepts a gas cartridge 124, which is inserted with its neck side toward the opening of the handle 104. A membrane 124*a* on the gas cartridge 124 is punctured by a beveled hypodermic syringe-type projection 140 in the puncture head 108 when the handle 104 and housing 102** are mated.

Still referring to FIG. 1, the system 100 further comprises a pneumatic cylinder 110, a trigger 112, an aerosol pressure line 118, and a pneumatic cylinder pressure line 120 (shown in phantom). The trigger 112 is connected to and movable within the main housing 102, and is operably connected to, and is in-line with, the aerosol pressure line 118 and the pneumatic cylinder pressure line 120 so as to allow for momentary "on" in those pressure lines 118 and 120.

The aerosol dispensing system 100 further comprises an aerosol pressure regulator 122. The projection 140 that pierces the gas cartridge 124 is connected to a lumen 142, which connects the aerosol pressure regulator 122 and the pneumatic cylinder pressure regulator 106. The aerosol pressure regulator 122 and the pneumatic cylinder pressure regulator 106 are housed within the main housing 102. The aerosol pressure line 118 is connected to the aerosol pressure regulator 122 at a first end **118*a* and the aerosol mixing head 116 at a second end 118*b*. The pneumatic cylinder pressure line 120 is connected at a first end 120*a* to the pneumatic cylinder pressure regulator 106 and to the input of the pneumatic cylinder 110 at a second end 120*b*. An optional pressure adjustment 136 located within the main housing 102 is connected to the aerosol pressure regulator 122 and the pneumatic cylinder pressure regulator 106 to adjust the outlet pressure of both regulators 122 and 106**.

The system 100 comprises one or more syringe barrels 114, permanently or releasably attached to the main housing 102, an aerosol mixing head 116, and a syringe manifold 130. The manifold 130 comprises individual lumens **130*a* that connect the individual syringe barrels 114 to the mixing head 116. The lumens 130*a* converge at a syringe outlet 131, which is in communication with the aerosol mixing head 116**.

The system 100 has a plunger coupler 126 for connecting one or more syringe plungers 128 to the pneumatic cylinder 110. A safety lock 132 is affixed to the main housing 102 and interacts with a lock notch 134 to allow or prevent movement of the syringe plungers 128. The syringe plungers 128 axially slide within the syringe barrels 114 and provide a seal so that the substances contained within the barrels 114 are prevented from escaping past the syringe plungers 128 (see also FIG. 4). Preferably, the pneumatic cylinder 110 is attached to the exterior of the main housing 102. The plunger coupler 126 is coupled, permanently or releasably, to the movable rod 127 of the pneumatic cylinder 110 and to the back end 129 of the syringe plungers 128.

The pneumatic power could also be obtained by a gas line (not shown) to an external pressurized gas source (not shown), rather than using the gas cartridge 124. The gas cartridge 124 can be of the standard type used for pellet guns, paintball guns, airbrushes, and the like. The typical gas cartridge approximately holds between 5 to 100 grams of gas and, more preferably, holds a range of 10 to 25 grams of gas. Preferably, the gas will be carbon dioxide, air, nitrogen, argon, nitrous oxide, or another inert gas. Typically, carbon dioxide will exist partially in the liquid phase when the pressure exceeds 850-PSI and is exposed to temperatures around 70-degrees Fahrenheit. Therefore, if carbon dioxide is used, the carbon dioxide cartridges will typically contain gas and liquid at a pressure of around 860-PSI. Nitrogen and air filled cartridges can be obtained commercially with pressures of 1800 PSI or higher. The pressure regulators 122 and 106 can be designed to use a first stage to step down the high pressure of the gas cartridge 124 to an intermediate pressure, 150 PSI for example, and then use a second stage to step down the intermediate pressure to the final operating pressure, expected to be in the range of 10 to 20 PSI. The pressure adjustment 136 can be a variable venturi or needle valve with a relief or bypass. Alternatively, the pressure adjustment 136 is eliminated from the system and the pressure level can be pre-set at an optimum value. Thus, there are no user operable controls for pressure adjustment, which is especially useful for non-critical applications or applications where the need for the lowest possible cost is a major consideration.

The aerosol spray dispenser or apparatus thus comprises a gas pressure source that is contained within the dispenser, wherein the entire dispenser apparatus is portable, without any connections to external power or gas supplies. Preferably, the system 100 is hand-held, wherein the trigger 112 is configured for depression and operation by the index finger of a user. The entire assembly 100 is ergonometric, lightweight, easy to hold, and to operate.

Figure 2:
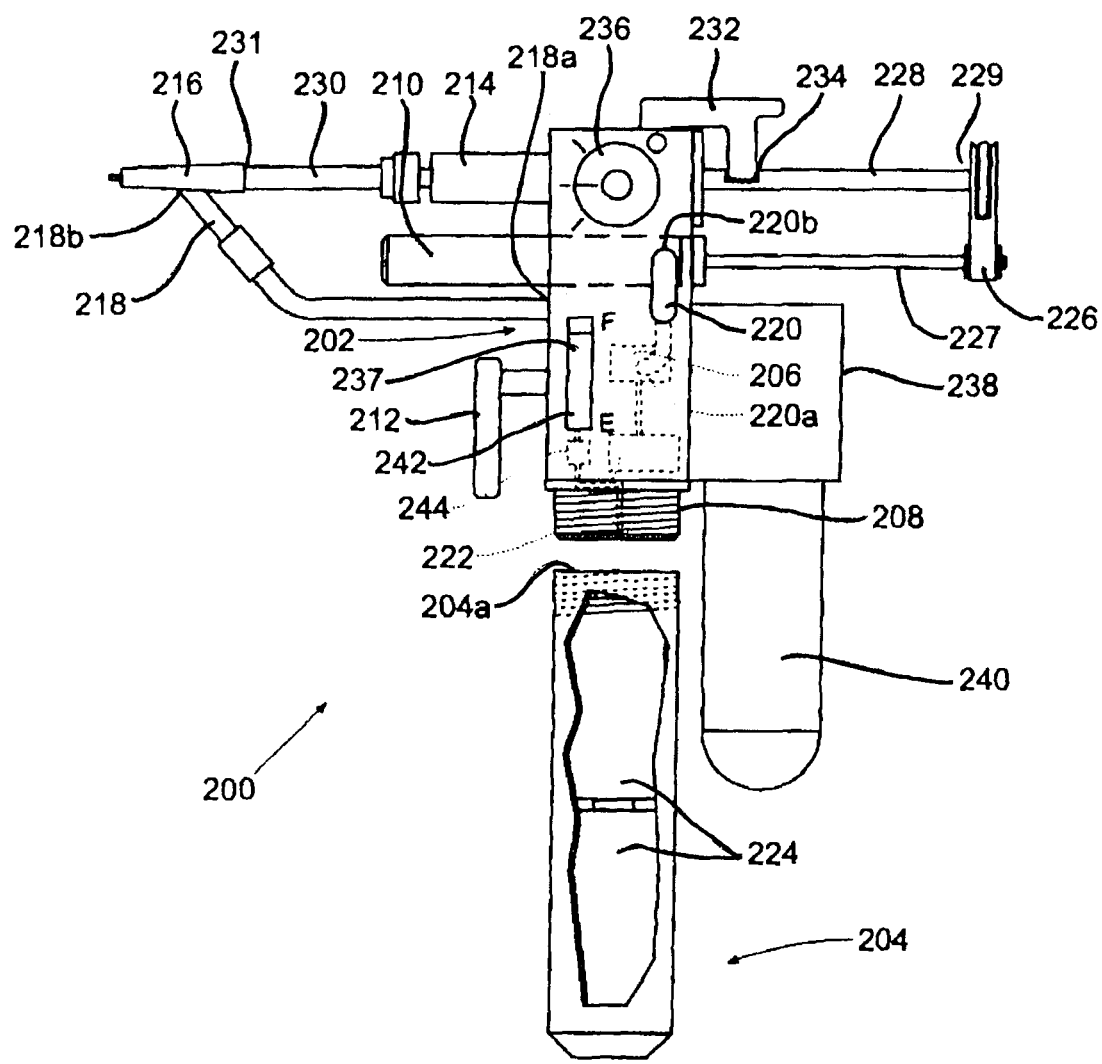
FIG. 2 illustrates a side, partially cut-away view of an aerosol applicator comprising an electrical power source and a dual syringe reservoir, according to an embodiment of the invention.

FIG. 2 illustrates a side view of an electrically powered aerosol dispenser system 200. The principles of the dispenser 200 are similar to those of the dispenser 100, except the power source and pressure arrangement has been modified. The aerosol dispensing system 200 comprises a main housing 202 and a handle/battery compartment 204. The housing 202 further comprises an air cylinder pressure regulator 206 (shown in phantom). The housing 102 the main housing 202 is mated with and in electrical communication with a battery compartment attachment 208. The handle/battery compartment 204 preferably threads onto the battery compartment attachment 208 and houses a battery or batteries 224. An opening 204a in the handle 204 accepts the batteries 224 for proper electrical contact and insertion within the handle 204.

The system 200 also comprises a pneumatic cylinder 210, a trigger 212, an aerosol pressure line 218, and a pneumatic cylinder pressure line 220. The trigger 212 is connected to and axially movable within, the main housing 202.

The electrical aerosol dispensing system 200 further comprises an aerosol pressure regulator 222 (shown in phantom). The aerosol pressure regulator 222 and the pneumatic cylinder pressure regulator 206 are located within the main housing 202 and are connected to the gas output of a pressure reservoir 240. The system 200 also comprise a pressure adjustment 236, and a charge indicator 242. A power controller 244 is electrically connected to the battery compartment 208 and, also, to an electrical pneumatic pump 238. An on-off switch (not shown) may be inserted between the electrical connection between the battery compartment attachment 208 and the electrical pneumatic pump 238. The pressure reservoir 240 is connected to the gas outlet of the electrical pneumatic pump 238. The pressure reservoir 240 may be affixed to either the main housing 202 or to the electric pneumatic pump 238. The power controller 244 is preferably housed within the main housing 202.

One or more syringe barrels 214 are releasably or permanently attached to the main housing 202 and are in fluid communication with an aerosol mixing head 216. A syringe manifold 230 having an outlet 231, similar to the manifold 130 (FIG. 1) connected the syringe barrels and the aerosol mixing head 216.

Referring further to FIG. 2, the system has a plunger coupler 226 permanently or releasably attached to a movable rod 227 of the pneumatic cylinder 210 and to the back end 229 of the syringe plungers 228. A safety lock 232 affixed to the main housing 202 interacts with a lock notch 234, to allow or prevent movement of one or more of the syringe plungers 228. The syringe plungers 228 are slideably constrained to move axially within the syringe barrels 214 and prevent any substances contained therein from escaping past the syringe plungers 228.

The pneumatic cylinder 210 is affixed to the exterior of the main housing 202. The aerosol pressure line 218 is connected to the aerosol pressure regulator 222 at a first end 218a and to the aerosol mixing head 216 at a second end 218b. The pneumatic cylinder pressure line 220 is connected at a first end 220a to the pneumatic cylinder pressure regulator 206 and to the input of the pneumatic cylinder 210 at a second end 220b. The trigger 212 is connected to, and is in-line with, the aerosol pressure line 218 and the pneumatic cylinder pressure line 220 so as to allow for momentary "on" in the pressure lines 218 and 220. The pressure adjustment 236 is connected to the main housing 202 with an interface control panel 237 exposed on the exterior of the main housing 202, and is in communication with the aerosol pressure regulator 222 and the pneumatic cylinder pressure regulator 206 to provide adjustment of the outlet pressure of both regulators 222 and 206. The charge indicator 244 is affixed to either the main housing 202 or the handle/battery compartment 204 and is electrically connected to the positive and negative terminals of the batteries 224.

Alternatively, the electrical power can be obtained by a power cord (not shown) connected to an external power source (not shown), rather than using the batteries 224. While any battery arrangement is possible in the present invention, preferably the batteries 224 provide direct current power ranging from 1.5 to 24 volts, and, more preferably, in the range of 3 to 18 volts. The pressure reservoir 240 is optional but is a preferred embodiment. The operating pressure range of the electrically powered system 200 is within the range specified for the operating pressure of the pneumatically powered dispenser 100 illustrated in FIG. 1. The pressure adjustment 236 is optional and can be either an adjustable venturi or needle valve with a relief, or it can be an electrical volume control to control the speed of the electric pneumatic pump 238. Alternatively, a single pressure adjustment 236, providing a single delivery rate, is sufficient for many uses.

Figure 3:
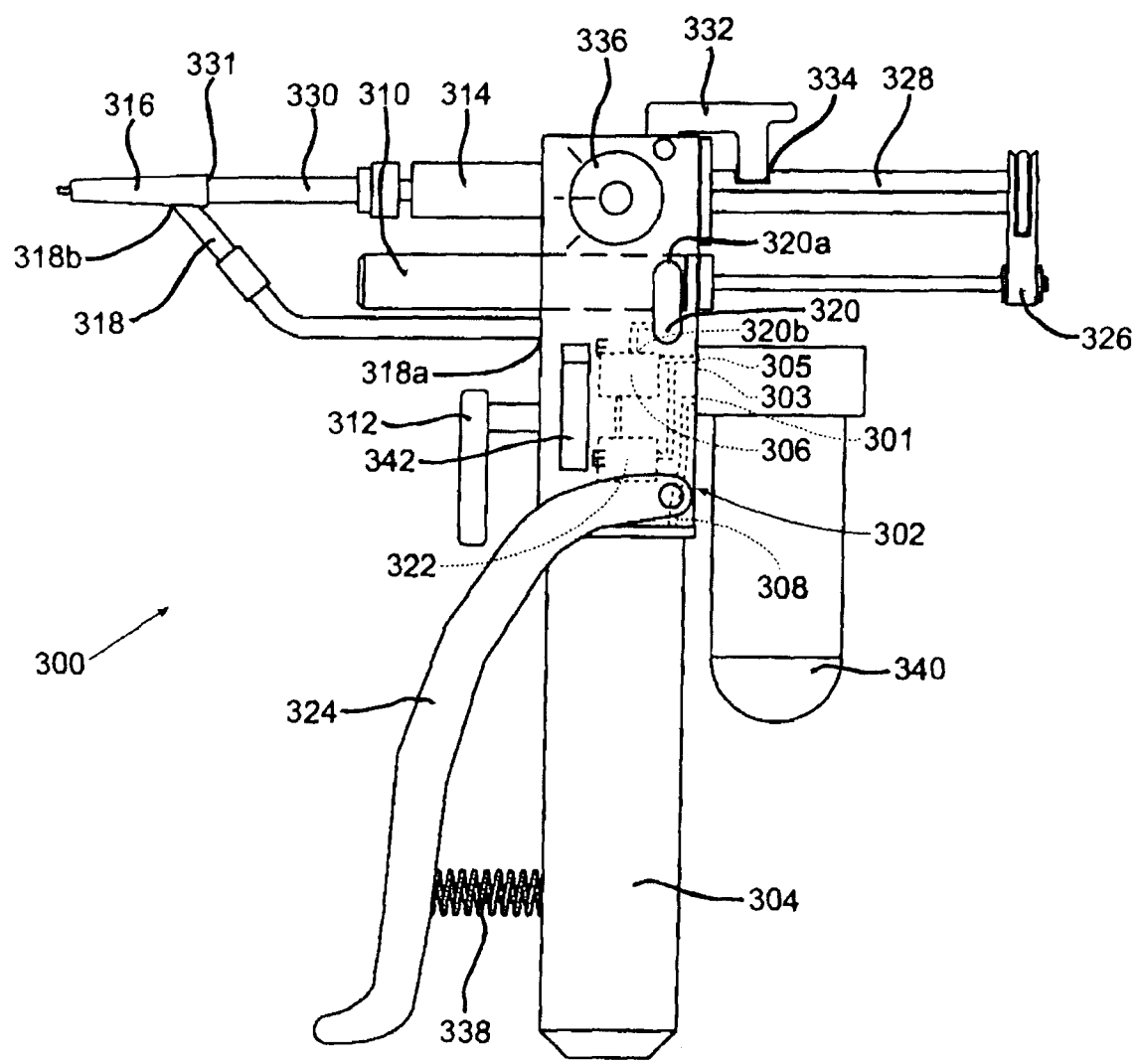
FIG. 3 illustrates a side view of an aerosol dispenser comprising a manual power source and a dual syringe reservoir, according to an embodiment of the invention.

FIG. 3 illustrates a side view of a manually powered aerosol dispenser system 300. The manual aerosol dispensing system 300 comprises a main housing 302, a handle/air pump 304, a pneumatic cylinder pressure regulator 306, a pneumatic cylinder 310, a trigger 312, one or more syringe barrels 314 permanently or releasably attached to the top portion of the main housing 302, an aerosol mixing head 316, an aerosol pressure line 318, and a pneumatic cylinder pressure line 320. The manual aerosol dispensing system 300 further comprises an aerosol pressure regulator 322, a pump lever 324, a plunger coupler 326, one or more syringe plungers 328, a syringe manifold 330, a safety lock 332, a lock notch 334, a pressure adjustment 336, a return spring 338, a pressure reservoir 340, and a pressure gauge 342.

Still referring to FIG. 3, the main housing 302 is affixed to the handle/air pump 304. The top of the main housing 302 is affixed to the syringe barrels 314, either permanently or releasably. The trigger 312 is affixed to, and constrained so that at least a part of the trigger moves axially within, the main housing 302. The handle/air pump 304 contains the air pump (not shown). The outlet 308 of the handle/air pump 304 is connected to the air inlet 301 of the pressure reservoir 340. The air outlet 303 of the pressure reservoir 340 is connected to the air inlet 305 of the main housing 302. The pressure reservoir 340 may be affixed to the main housing 302 or to the handle/air pump 304. The aerosol pressure regulator 322 and the pneumatic cylinder pressure regulator 306 are housed within the main housing 302 and communicate with the air inlet 305 of the main housing 302. Any suitable linkage arrangement connects the pump lever 324 with an air pump mechanism (not shown) housed within the handle/air pump 304. The pump lever 324 is pivotably affixed to either the main housing 302 or the handle/air pump 304. The return spring 338 is affixed between the handle/air pump 304 and the pump lever 324.

The safety lock 332 interacts with the lock notch 334 on one or more of the syringe plungers 328. The syringe plungers 328 axially slide within the syringe barrels 314 and prevent any substances contained therein from escaping past the syringe plungers 328. The syringe barrels 314 are connected to the syringe manifold 330, which has an outlet 331 communicating with the aerosol mixing head 316. The pneumatic cylinder 310 is affixed to the exterior of the main housing 302. The aerosol pressure line 318 is in fluid communication with the outlet of the aerosol pressure regulator 322 at a first end 318a and connected to the inlet of the aerosol mixing head 316 at a second end 318b. The pneumatic cylinder pressure line 320 is connected at a first end 320a to the outlet of the pneumatic cylinder pressure regulator 306 and to the input of the pneumatic cylinder 310 at a second end 320b. The plunger coupler 326 is permanently or releasably affixed to the movable rod of the pneumatic cylinder 310 and to the back end of the syringe plungers 328. The trigger 312 is connected to, and is in-line with, the aerosol pressure line 318 and the pneumatic cylinder pressure line 320 so as to allow for momentary "on" in the pressure lines 318 and 320. The pressure adjustment 336 is affixed to the main housing 302 and is in communication with the aerosol pressure regulator 322 and the pneumatic cylinder pressure regulator 306 to provide adjustment of the outlet pressure of both regulators 322 and 306. The pressure gauge 342 is affixed to either the main housing 202 or the handle/air pump 304 and is connected to the air outlet of the pressure reservoir 340, possibly with an electrical connection.

Referring further to FIG. 3, power for the system 300 is generated by repetitively squeezing the pump lever 324 toward the handle/air pump 304. The pump lever 324 is biased away from the handle/air pump 304 by the return spring 338 and thus is ready for another pump cycle when released. The manual air pump can provide air pressure ranging from 10 to 500 PSI, and preferably in the range of 20 to 200 PSI. In a preferred embodiment, the pressure reservoir 340 is designed to store air and permit a buildup of pressure for even pressure delivery so that an immediate drop off of pressure will not occur when the trigger 312 is depressed. The operating pressure range of the manually powered system 300 is generally lower than the range specified for the operating pressure of the pneumatically powered dispenser 100 illustrated in FIG. 1. The pressure adjustment 336 is optional and can be either an adjustable venturi or needle valve with a relief, a single pressure adjustment, providing a single delivery rate and without user adjustability.

The syringe plungers may alternatively be moved with a lever, such as the pump lever 324 or the trigger 312, rather than using the pneumatic cylinder 310 to generate the force, possibly with a common ratchet or pawl arrangement.

FIG. 4 illustrates a partially cut-away, top view of an aerosol dispenser 400 comprising a single syringe mixing system that could be integrated into any of the arrangements and embodiments of the previous figures. The mixing aerosol dispensing system 400 comprises a main housing 402, a mixing syringe barrel 406, a syringe bypass channel 404, a separator plunger 408, a pneumatic cylinder 410, a pneumatic cylinder pushrod 412, one or more non-mixing syringe barrels 414, an aerosol mixing head 416, an aerosol pressure line 418, and a pneumatic cylinder pressure line 420. The system 400 further comprises one or more syringe plunger gaskets 422, a plunger coupler 426, one or more syringe plungers 428, a syringe manifold 430, a pressure adjustment 436, a liquid component 438, a dry component 440, a liquid component 442, one or more one way check valves 444, a disconnected plunger 446 and a plunger arm 448.

Still referring to FIG. 4, the preferred drive system for the mixing syringe system 400 is the same as that described for FIG. 1, 2, or 3. The mixing syringe barrel 406 is filled with the dry component 440 in its front half and with the liquid component 438 in its back half. The two components 438 and 440 are separated by the separator plunger 408. The non-mixing syringe barrel 414 is filled with liquid component 442. The one way check valves 444 are affixed to the front of the non-mixing syringe barrel 414 and the mixing syringe barrel 406 to prevent air from flowing retrograde back into the syringe barrels 414 and 406 and prematurely aging or damaging the components 440 and 442. The one way check valves 444 allow for flow from the syringe barrels 414 and 406 to the manifold 430, but prevents fluid from flowing back into the barrels 406 and 414, which minimizes potential clotting and clogging. An additional valve, such as a stopcock (not shown), can further be added to the outlets of the syringe barrels 414 and 406 or the syringe manifold 430, which is affixed between the syringe barrels 414 and 406 and the aerosol mixing head 416.

When the pneumatic cylinder 410 is pressurized by air pressure in the pneumatic cylinder pressure line 420 (shown in phantom) as previously described, the pneumatic cylinder pushrod 412 forces the plunger coupler 426 and the syringe plungers 428 toward the aerosol mixing head 416. Thus, the elastomeric gaskets on the distal ends of the syringe plungers 428 move toward the distal end or front of the syringe barrels 406 and 414. The separator plunger 408 will advance until its proximal end has passed beyond the proximal end of the bypass channel 404 in the mixing syringe barrel 406. The disconnected plunger 446 remains as a seal for the liquid component 442 and only moves when the plunger arm 448 makes contact with the disconnected plunger 446. The plunger arm 448 begins pushing the disconnected plunger 446, and the liquid component 438 is forced under pressure through the bypass channel 404 and into the front portion of the mixing syringe barrel 406 where it combines with dry component 440. The incorporation of several bypass channels 404 could be utilized to enhance mixing, but unless passive mixing occurs, the mixing may also be done by shaking the system to combine components 438 and 440. The combined components 438 and 440 are now a liquid with a viscosity substantially similar to that of water, 1.0 centipoise (cp).

Additional pressure causes the syringe plungers 428 to continue advancing and the combined liquid component 438 and dry component 440 is ejected into the syringe manifold 430 along with the liquid component 442, which also preferably has a viscosity approximately similar to that of water. The components 438+440 and 442 are injected into the aerosol mixing head 416 where they are jetted into a high-pressure air stream powered by the aerosol pressure line 418 which is connected to the aerosol mixing head 416 from the bottom or side, as described with respect to the pressure lines 118, 218, and 318. The high-pressure air jet further helps mix and atomize the components, which are carried into a spray pattern, with the preferred pattern being a solid cone. Additional seals can be used to enhance shelf life of the product as can additional valves. Furthermore, detents, locks, and ratchets can be used to control the advancement of the syringe plunger 428, for example, stopping the plungers 428 at the bypass channel 404 and later at designated 1-cc volume stages, so that multiple 1-cc volume boluses of liquid from each syringe can be dispensed. The pressure adjustment 436 can be used to change the spray pattern and level of mixing for any specific arrangement as desired.

Figure 5:
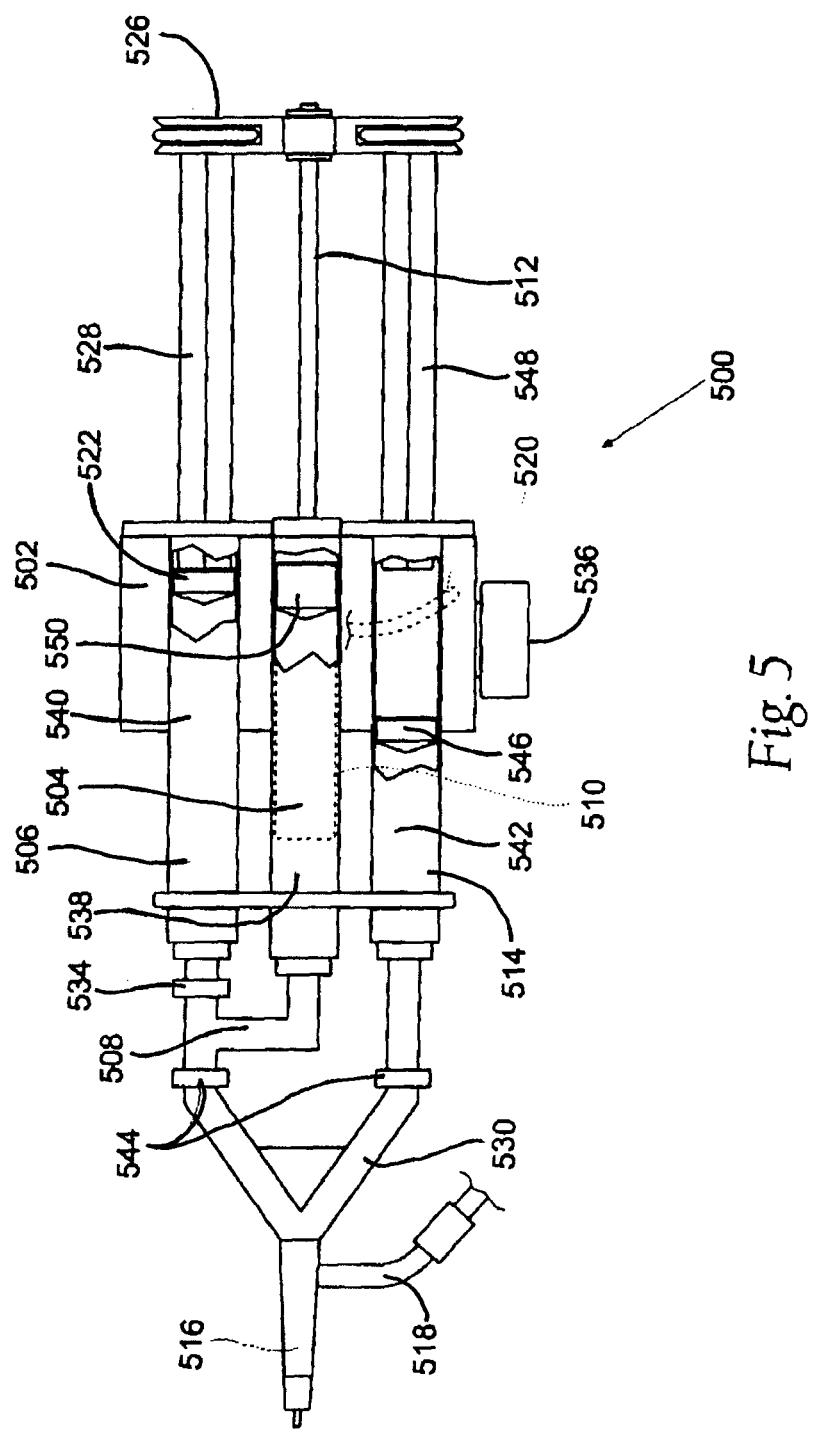
FIG. 5 illustrates a top, partial cutaway view of an alternate aerosol dispenser comprising a multiple syringe mixing system and a mixing manifold.

FIG. 5 illustrates a top view of an alternate aerosol dispenser 500 comprising a multiple syringe mixing system. The system 500 will operate to mix compounds as described with respect to FIG. 4, but with each individual component housed in an individual syringe barrel. The multiple syringe mixing aerosol dispensing system 500 comprises a main housing 502, a mixing syringe barrel 506, a storage syringe barrel 504, a mixing manifold 508, a mixing reverse flow check valve 534, a pneumatic cylinder 510, a pneumatic cylinder pushrod 512, one or more non-mixing syringe barrels 514, an aerosol mixing head 516, an aerosol pressure line 518, and a pneumatic cylinder pressure line 520 (shown in phantom). The manual aerosol dispensing system 500 further comprises one or more syringe plunger gaskets 522, a plunger coupler 526, one or more syringe plungers 528, a syringe manifold 530, a pressure adjustment 536, a liquid component 538, a dry component 540, a second liquid component 542, one or more forward flow one-way check valves 544, a disconnected plunger 546, a plunger arm 548, and a passive plunger 550.

The disconnected plunger 546 keeps the second liquid component 542 within the non-mixing syringe barrel 514. The mixing syringe barrel 506, the storage syringe barrel 504, and the non-mixing syringe barrel 514 are all shown in partial cutaway view to show internal details. The plunger arm 548 normally is disconnected from the disconnected plunger 546 and will move the disconnected plunger 546 when contact between the two is made. The plunger arm 548 and the syringe plunger 528 are connected to the plunger coupler 526 and move in unison, driven by the pneumatic cylinder pushrod 512 and the pneumatic cylinder 510. Any variations in volume delivered for a given chemical component are generated by changing the diameters of one or more of the syringe barrels 514 and 506.

The plunger coupler 526 and respective plungers 528 and plunger arms 548 are initially provided in the forward or distal most location that provides for the specified volume of components in the syringe barrels 514 and 506. The plunger coupler 546 is withdrawn proximally until it stops in order to mix the components. Liquid component 538 is withdrawn from the storage syringe barrel 504 through the mixing manifold 508 and mixing check valve 534 into the mixing syringe barrel 506, where it mixes with dry component 540. The pneumatic cylinder pressure line 520 is then pressurized causing the pneumatic cylinder 510 to retract the pneumatic cylinder pushrod 512, the plunger arm 548 and the plunger coupler 526 distally. The syringe plungers 528 and plunger arms 548 move forward at a rate determined by the pressure exerted on the pneumatic cylinder 510, the area of the pneumatic cylinder 510 piston (not shown), and the friction in the system. The two liquid components are forcibly ejected through the forward flow one-way check valves 544, through the syringe manifold 530, and into the aerosol head 516, where gas under pressure is injected through the aerosol pressure line 518 to nebulize, atomize, or otherwise spray and mix the components.

Figure 6:
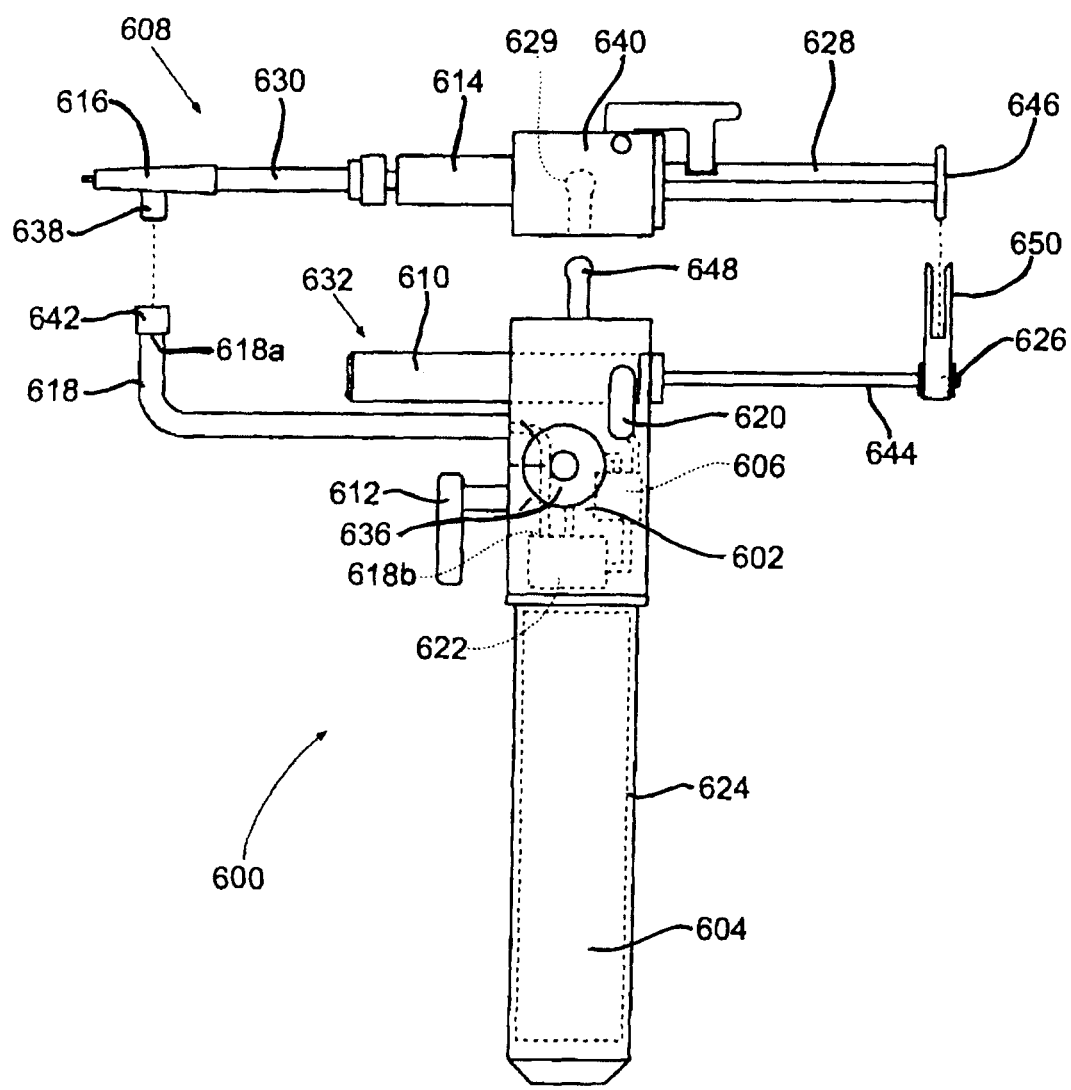
FIG. 6 illustrates a side view of an aerosol dispenser comprising a reusable dispenser and a disposable syringe reservoir system, according to an embodiment of the invention.
Figure 7:
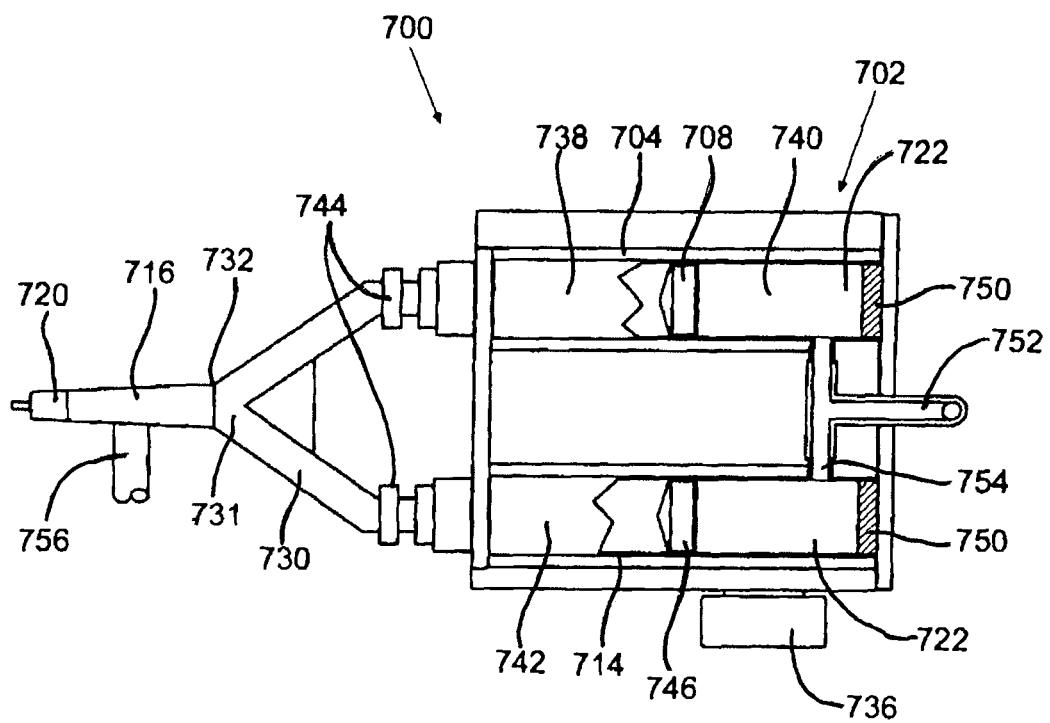
FIG. 7 illustrates a top, partially cut-away view of a pneumatically driven aerosol dispenser comprising a dual tank system without a separate pneumatic cylinder, according to the present invention.

FIG. 6 illustrates a side view of an aerosol sealant applicator 600 comprising a detachable, disposable syringe head 608 and a reusable dispenser 632. The system 600 functions similar to the previous systems depicted in FIGS. 1, 2, and 3. The detachable, disposable syringe head 608 comprises a syringe bracket 640, an attachment slot 629, a plurality of syringe plungers 628, a plurality of plunger flanges 646, a plurality of syringes 614, a syringe manifold 630, an aerosol mixing head 616, and an aerosol fitting 638. The reusable dispenser 632 comprises a main housing 602, an attachment prong 648, an aerosol pressure line 618, an aerosol pressure coupler 642, a pneumatic cylinder 610, a pneumatic cylinder pushrod 644, and a pneumatic cylinder pressure line 620. The reusable dispenser 632 further comprises a trigger 612, a pressure adjustment 636, a gas cartridge 624, a handle 604, an aerosol pressure regulator 622, one or more plunger coupler slots 650 and an air cylinder pressure regulator 606.

Still referring to FIG. 6, the disposable syringe head 608 is configured for easy, secure attachment to, and detachment from, the main housing 602 and the plunger coupler 626. Quick connect fittings such as the attachment prong 648, which is affixed to the main housing 602 are configured to be inserted into and latch with the attachment slot 629, which is integrally affixed to the syringe bracket 640. The flanges 646 on the proximal end of the syringe plungers 628 slide into slots 648 in the plunger coupler 626. The plunger coupler is affixed at or near the proximal end of the pushrod 644. The pushrod 644 is affixed to a piston (not shown) within the pneumatic cylinder 610 and moves when differential pressure is applied thereon. The pneumatic cylinder 610 is affixed to the main housing 602. The pneumatic cylinder pressure line 620 is connected at a first end to the pneumatic cylinder 610. In this embodiment, a reverse acting pneumatic cylinder 610 is used and the air cylinder pressure line 620 is affixed to the proximal end of the housing of the pneumatic cylinder 610. The pneumatic cylinder pressure line 620 is connected at its other end to the output of the air cylinder pressure regulator 606. The aerosol pressure line 618 is connected at a first end 618a to the aerosol pressure regulator 622 and at a second end 618*b* to an aerosol pressure coupler 642. The aerosol pressure coupler 642 is a quick connect that seals to the aerosol fitting 638, which is affixed, and operably connected, to the aerosol mixing head 616. The syringes 614 preferably can be standard syringes ranging in size from 0.25-cc to 60-cc, or they can be lyophilizing syringes, mixing syringes, or the like.

The aerosol pressure regulator 622 and the air cylinder pressure regulator 606 may be the same device or they can be separate devices. They can have a common pressure source or they can operate as a two-stage pressure regulator where, for example, the aerosol pressure regulator 622 serves as the first stage and lowers the pressure to, for example, 30 PSI. The pneumatic cylinder pressure regulator 606 can then serve as the second stage and drop the pressure from 30 PSI to 12 PSI, for example. The pressure adjustment 636 can control the spring loading on a diaphragm adjust a needle valve in one or both of the regulators 622 and 606. Such values of pressure are appropriate for a 5⁄16-inch diameter pneumatic cylinder, while a larger diameter pneumatic cylinder can operate with lower pressures. The pressure adjustment 636 is affixed with its control surface externally affixed to the main housing 602. The main housing 602 and the air regulators 622 and 606 can be fabricated from polymers such as, but not limited to, ABS, polyolefin, PVC, polysulfone, polyamide, or the like or they can be fabricated from metal. Spring devices can be fabricated from spring metals such as, but not limited to, stainless steel 304, nickel cobalt alloys, titanium, nitinol, or the like.

The regulators 606, 622 are preferably affixed within the main housing 602 although they could also be affixed externally thereto or about the handle 604. The trigger 612 is operably connected to a valve in either the inlet or outlet line to the regulators 606 and 622 so that depressing the trigger 612 opens the valve momentarily to operate the aerosol applicator. The trigger 612 is affixed to move axially within the main housing 602 or the handle 604. The trigger can have a spring return (not shown) to restore it to an "off" position when manual force is removed. Snapping the attachment prong 648 into the attachment slot 628 automatically aligns and connects the syringe flanges 646 within the slots 650 in the plunger coupler 626 while the aerosol fitting 638 snaps and seals into the aerosol pressure coupler 642. Thus, the disposable syringe assembly 608 can be maintained sterile in single or double barrier aseptic packaging, be unpacked, and then be snapped onto the aerosol spray device 632. The gas cartridge 624 (shown in phantom) is captured within the handle 604, as described with respect to FIG. 1 and the gas cartridge 124. In another embodiment, the pneumatic cylinder 610 is replaced with a hydraulic cylinder and a hydraulic fluid source (not shown), which is pressurized by the gas outlet of the pneumatic cylinder pressure regulator 606. The entire assembly 600 can be supplied as a sterile assembly. Examples of possible sterilization processes include being steam sterilized, ethylene oxide sterilized, electron beam sterilized, or gamma irradiated with a source such as cobalt 60. The assembly 600 can be packaged in a PETG tray with a Tyvek® lid and then have an optional, second pouch sealed to enclose the sealed tray. This same packaging can be used for the disposable syringe assembly 608, as well, either separately or in one packaging.

FIG. 7 illustrates a top view of a pneumatically driven aerosol dispenser 700 comprising a dual tank system without a separate pneumatic cylinder. The aerosol dispenser 700 comprises a main body 702, a plurality of slots 704 within the main body 702, a plurality of disconnected syringe plungers 708, a plurality of syringe barrels 714 shown in partial cutaway view, a mixing head 716, an aerosol spray tip 720, a plurality of syringe pressurization volumes 722, a syringe manifold 730, a bolus of sealing compound component 738, a pressure adjustment 736, a bolus of sealing compound component 742, a plurality of one way check valves 744, a plurality of syringe barrel end seals 750, a syringe barrel pressurization manifold 752, a plurality of syringe barrel inlet ports 754, and an aerosol pressure line 756.

The main body 702 comprises slots 704, which are integral to the main body 702, or are created by separate external structures such as clips, brackets, or clamps, affixed to the main body 702. The syringe barrels 714, of which two are used in this embodiment, contain the two liquid components 738 and 742. The disconnected syringe plungers 708 reside within the inner lumen of the syringe barrels 714 and separate the liquid components 738 and 742 from air or other contaminants. At one end, the one-way check valves 744, which are connected within the line between the syringe manifold 730 and the syringe barrels 714, prevent retrograde flow of contaminants back into the syringe barrels 714. The outlet 731 of the syringe manifold 730 is connected to the inlet 732 of the mixing head 716. The aerosol spray head 720 is attached to the mixing head 716, which is also connected to the aerosol pressure line 756. The aerosol pressure line 756 is connected to a pressurized gas source (not shown), as has been described with the previous drawings and embodiments. The syringe barrel end seals 750, of which one is used on each syringe barrel 714, are affixed at the proximal end of each syringe barrel 714 and prevent the ingress or exit of fluids from or into the syringe barrels 714. The syringe pressure inlet line 752 is connected at one end to the syringe barrel inlet ports 754 and at the other end to a pneumatic pump, pneumatic pressure regulator, pneumatic air supply, hydraulic fluid supply, or the like, similarly as described with respect to the previous drawings and embodiments.

When gas or fluid pressure increases in the pressurization regions 722, the disconnected syringe plungers 708 move distally to force the components 738 and 742 to be separately ejected through separate channels in the distal end of the syringe barrels 714. The two components 738 and 740 are next forced through the separate one way check valves 744, through the separate paths of the manifold 730 and into the aerosol mixing head 716 where the two components 738 and 742 are jetted into space and mixed with air being jetted from the aerosol pressure line 756. No mixing occurs within the confines of the dispenser 700 until the components enter the mixing head 716, and, thus, the chance of the components 738 and 742 mixing, gelling, and clogging the system is minimized. The disconnected syringe plungers 708 are configured to seal against the syringe barrel 714 inner walls and to move axially within the syringe barrels 714. The plungers 708 are preferably fabricated from polymeric materials with no permeability and with at least a small amount of elastomeric resilience to provide a good seal. The perimeter of the plungers 708 can comprise ridges and valleys running circumferentially to enhance the seal against the syringe barrel 714. The length of the plunger 708 is preferably at least as long as its diameter and preferably 1.5 to 2 times the diameter. It is advantageous to configure the plungers 708 to have a conical distal end to improve movement under pressure. By this configuration, it is possible to eliminate a pneumatic cylinder, such as the pneumatic cylinder 110 from the embodiment shown in FIG. 1. The use of hydraulic fluid, or liquid, can improve the performance of the system relative to a pneumatic fluid, since the hydraulic fluid has no compressibility and a specific volume of hydraulic fluid movement causes positive displacement within the syringe plungers 708.

Figure 8:
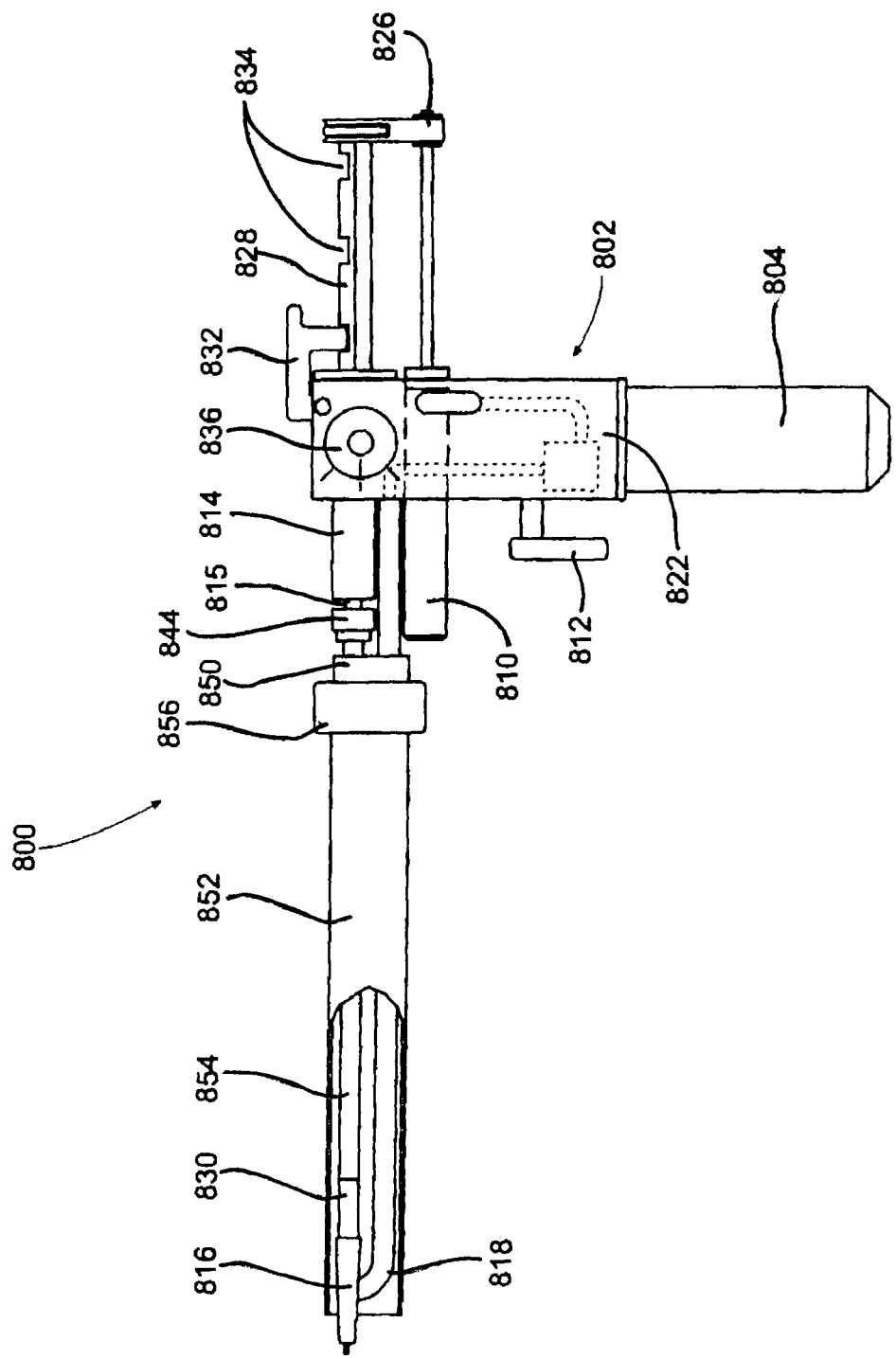
FIG. 8 illustrates a side, partially cut-away view of an aerosol dispenser adapted for insertion and use through a laparoscopic sheath or trocar, according to an embodiment of the invention.

FIG. 8 illustrates side view of an aerosol dispenser system 800 adapted to be inserted through a laparoscopic trocar or sheath 852. The laparoscopic aerosol dispenser system 800 comprises a main body 802, a handle 804, a pneumatic cylinder 810, a trigger 812, a plurality of syringe barrels 814, an aerosol spray tip 816, an aerosol pressure line 818, a pressure regulator 822, a syringe plunger coupler 826, a plurality of syringe plungers 828, a syringe manifold 830, a pressure adjustment 836, a plurality of one way check valves 844, a laparoscopic sheath seal 850, the laparoscopic sheath 852, a plurality of manifold extension lines 854, and a laparoscopic sheath hub 856.

The aerosol dispenser system 800 is configured for use on a patient (not shown) to deliver sealant compound internally, through laparoscopic access devices, commonly known as sheaths or trocars. Referring to FIG. 8, the aerosol spray tip 816 is affixed to the syringe manifold 830, which is connected to the manifold extension lines 854. The manifold extension lines 854 are connected at their proximal ends to the outlets of the syringe barrels 814. One-way check valves 844 are connected in the line somewhere between the outlet 815 of the syringe barrels 814 and the aerosol spray tip 816. The aerosol pressure line 818 is preferably parallel with and located as near the manifold extension lines 854 as possible to minimize the overall diameter of sheath tube 852 needed to encompass the assembly. The manifold extension lines 854, of which two are comprised by this embodiment, are likewise close together with minimum spacing to minimize diameter of the sheath tube 852. The inside diameter of the sheath tube 852 can range between 3 mm and 20 mm, with a preferred range of 8 mm to 15 mm. The length of the sheath tube 852 and sheath hub 856 ranges between 5 cm and 40 cm with a preferred range of 8 cm to 20 cm. The laparoscopic sheath seal 850 is affixed to the manifold extension lines 852 and aerosol pressure line 818. The sheath seal 850 prevents the escape of fluid, liquid and gas, proximal to itself when the laparoscopic sheath seal 850 is reversibly, or releasably, sealed against, or inside, the laparoscopic sheath hub 856. The assembly can further comprise endoscopes, video cameras, illumination light sources, and the like, all of which are not shown.

The other components of the aerosol spray dispenser 800 are located proximal to the sheath seal 850 and are located outside the laparoscopic sheath and the patient during use. The aerosol spray dispenser system 800 can use the pneumatic actuation as described in FIG. 1, it can use some or all of the components described in FIG. 2 or 3, or it can be a hybrid of any of the aforementioned. In another embodiment, the pneumatic cylinder 810 can be replaced with a hydraulic cylinder, the configuration of which would be almost identical to that of the pneumatic cylinder 810. Instead of gas, the hydraulic cylinder is pressurized with liquid such as oil, water, or the like. The source of pressurized hydraulic fluid can be another cylinder, reservoir, or tank, not shown. The hydraulic fluid is either pumped into the hydraulic cylinder using a positive pressure pump or positive displacement pump, or it is simply exposed to pneumatic pressure and flows under the influence of this pre-determined and controlled pressure. The hydraulic system may have advantages over the pneumatic system in terms of consistency, since the hydraulic fluid is incompressible and acts more like a positive displacement system than the compressible pneumatic system that is being driven with gasses such as, but not limited to, nitrogen, carbon dioxide, air, helium, or the like. Furthermore, in another embodiment, the system can be tailored to deliver material through a catheter, rather than a laparoscopic sheath. The catheter-based system requires the use of flexible aerosol pressure line 818 and a flexible manifold extension line 854.

Figure 9:
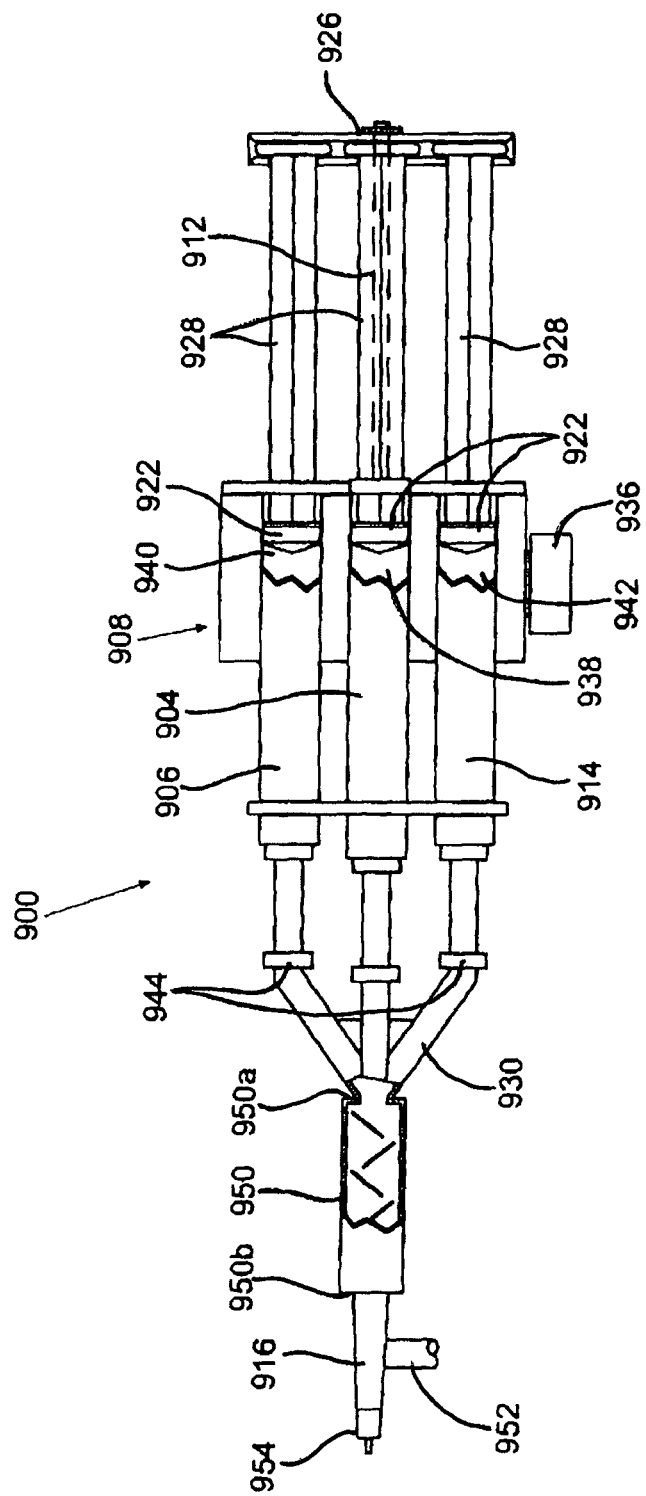
FIG. 9 illustrates a top, partially cut-away view of an aerosol dispenser comprising apparatus to pre-mix the sealant components prior to exiting the distal end of the dispenser and wherein a buffering solution is added just prior to spraying, according to an embodiment of the invention.

FIG. 9 illustrates a top view of an aerosol dispenser 900 comprising an apparatus to pre-mix the sealant components prior to exiting the distal end 954 of the dispenser 900, and wherein a buffering solution is added just prior to spraying. The aerosol dispenser 900 comprises a main housing 902, a buffering solution syringe barrel 904, a first component syringe barrel 906, a second component syringe barrel 914, a pneumatic cylinder (not shown), a pneumatic cylinder pushrod 912, an aerosol spray head 916, a plurality of syringe plunger gaskets 922, a plurality of syringe plungers 928, a syringe manifold 930, an optional pressure adjustment 936, a buffering solution 938, a liquid sealant component 940, a liquid sealant component 942, a plurality of one way check valves 944, a mixing chamber 950, and an aerosol pressure line 952.

The buffering solution 938 can be selected from materials including, but not limited to, TRIS, phosphate, bicarbonate, and the like. The liquid sealant component 940 and component 942 are preferentially stored at a pH of around 7.0, which provides for a very long gel time, on the order of 10 minutes (600 seconds) or more. When they are injected through the manifold 930 and mixed in the mixing chamber 950, it is beneficial to inject the buffering solution 938 to accelerate the gel time to be on the order of 5 seconds, which occurs at a resultant pH of around 8.5 to 9.0. If the total time of use for injecting three or more boluses of sealant from the dispenser 900 is less than the extended gel time, then the mixing chamber 950 and aerosol spray head 916 will not clog or become blocked. The injection of the buffering solution 938 can occur at the proximal end 950*a* of the mixing chamber 950, it can occur at the distal end 950*b* of the mixing chamber 950, or it can occur somewhere intermediate the proximal end 950*a* and the distal end 950*b* of the mixing chamber 950. The overall gel time needs to be set so that three or more boluses of sealant can be dispensed and not become gelled within the mixing chamber 950 or aerosol spray head 916. The mixing chamber 950 can comprise stators or mixing vanes that cause two or three separate materials to be moved laterally into the flow path of another chemical to enhance mixing.

The proportions of each component can advantageously be varied by advancing the syringe plungers independently, with independent or proportional control. The purpose of separate proportion control is to deliver a hydrogel having different properties such as gel time, gel strength, or degradation rate, appropriate and tailored for the intended use but with the same dispenser and components. A control dial can be comprised by the system which sets the individual rates of delivery according to simple descriptors such as "Fast Gel Time," "Slow Gel Time," "1-Week Degradation," "Adhesion Barrier," "Lung Sealant," and the like. In such an arrangement, the amount of buffering solution or sealant component delivered can be adjusted by advancing decoupled syringe plungers at separate rates of speed. To accomplish this, different pressures can be exerted on the decoupled syringe plungers or their separate, decoupled, driving pneumatic cylinders, motors, pumps, or the like. In yet another arrangement, the driving pneumatic cylinders, motors, pumps, and the like could further be coupled together, but geared to move at different speeds with a controllable gearbox to change the relative speeds. While certain limitations apply to the combinations of performance available with two components and a buffer solution, the addition of another, or fourth, syringe filled with water can be advantageous in providing greater range of performance characteristics. The amount of buffering solution delivered can be also adjusted by varying the relative diameter of the buffering solution syringe barrel 904 relative to the diameter of the syringe barrels 906 and 914 delivering the sealing compounds 940 and 942, respectively.

Referring again to FIG. 4, one syringe barrel 406 comprises both powdered, lyophilized PEG 438 and unbuffered albumin solution 440, which are separated by a separator plunger 408 and selectively connected by a bypass channel 404. The other syringe barrel 414 is filled with a buffering solution 442. It is beneficial to store a protein component, such as albumin solution or the like, at a pH of around 7.0 in order to avoid degradation and then raise the pH just before it is dispensed.

Alternatively, the syringe barrel 406 is filled with powdered, lyophilized PEG 438 and water or appropriate diluent 440, again separated by the separator plunger 408. In this arrangement, the other syringe 414 is filled with albumin 442. When the plunger coupler 426 is advanced, the separator plunger 408 pushes past the proximal end of the bypass channel 404 allowing the albumin or diluent 440 to flow forward and mix with the powdered PEG 438.

Cross-linking of the sealing compound components albumin and PEG4-SG occurs via nucleophilic substitution by a primary amine (lysine group) and a carbonyl (glutarate function). Albumin contains numerous amine groups that react readily with the carbonyl groups on each arm of a 4-arm PEG solution. The cross-linking reaction rate is dependent on the solution pH. For this reason, albumin is preferably buffered to a pH level that yields the desired gel time and gel strength. Increasing the pH causes amines to be more reactive. Cross-linking is very slow at pH levels typical of the bulk albumin (pH=6.8 to 7.2), but it does not entirely cease to occur. In an embodiment, the albumin is buffered with 90 millimoles of TRIS and approximately 20 millimoles of sodium carbonate. Batch variation of albumin requires carbonate to be titrated until the final pH is reached. This buffer is selected to achieve a gel time and gel strength needed for arterial closure. Other buffers can be used in other embodiments, resulting in slightly different gel times and gel strengths Some factors to be considered when selecting a buffer include: ability of the buffer to maintain the desired pH, compatibility with the final compound and delivery system, product safety, stability, cost, and buffer capacity, or strength. The buffer could also be a phosphate buffer, a carbonate buffer, a borate buffer, and CHES. Another factor to consider is the ability to blend the buffer into the component, or components, being buffered during the spraying. This ability is determined, in part, by the kinetics of buffering the sealing compound solution. Each buffer may require a different time to shift the pH of the solution.

Figure 10:
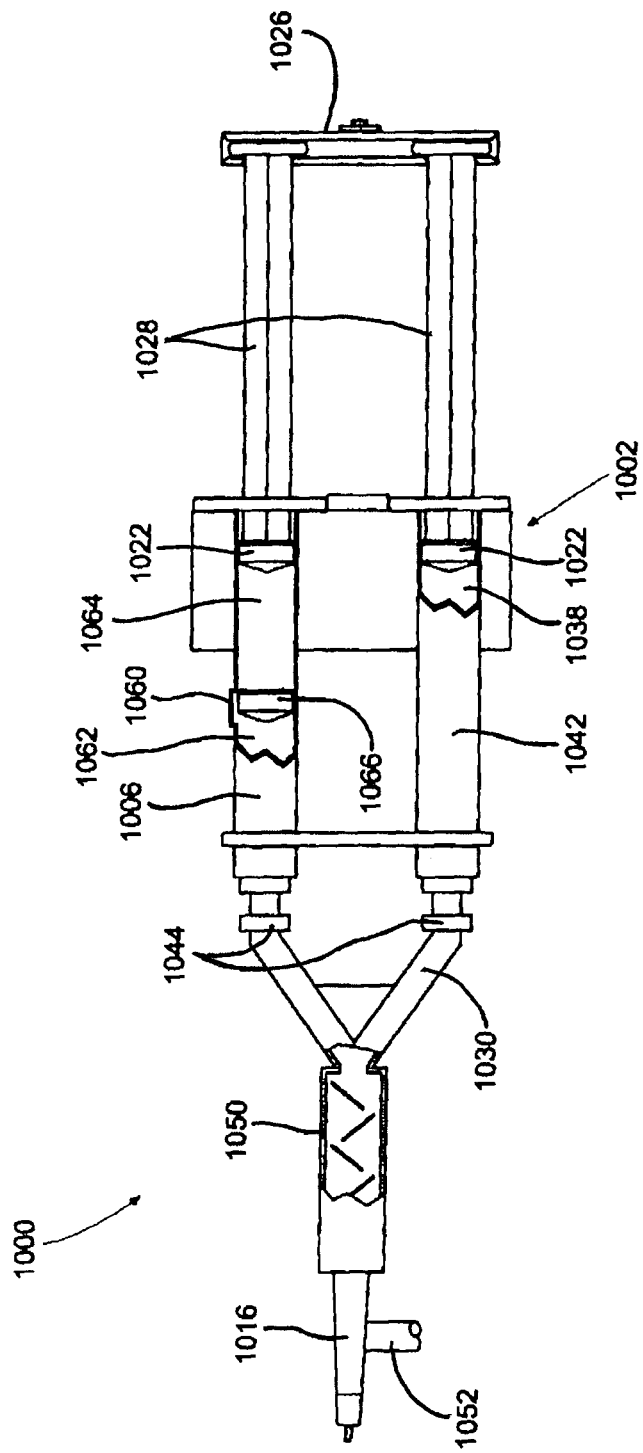
FIG. 10 illustrates a top, partially cut-away view of an aerosol dispenser comprising an apparatus to pre-mix the sealant components within one of the syringes and a second syringe to contain buffering solution, which is admixed with the sealant components to accelerate the gel reaction, according to an embodiment of the invention.

FIG. 10 illustrates a top, partial cutaway view of an aerosol dispenser 1000 comprising an apparatus to pre-mix the sealant components within one of the syringe barrels and wherein a buffering solution is added just prior to spraying. The aerosol dispenser 1000 comprises a main housing 1002, a mixing syringe barrel 1006, an aerosol spray head 1016, a plurality of syringe plunger gaskets 1022, a syringe plunger coupler 1026, a plurality of syringe plungers 1028, a syringe manifold 1030, a buffering solution 1038, a buffer syringe barrel 1042, a dry sealant component A 1062, a liquid sealant component B 1064, a plurality of one way check valves 1044, a mixing chamber 1050, and an aerosol pressure line 1052. The mixing syringe barrel 1006 further comprises a bypass channel 1060 and a detached plunger seal 1066.

Referring to FIG. 10, the mixing syringe barrel 1006 is divided into two chambers by the detached plunger seal 1066. The detached plunger seal 1066 is constrained to move axially within the mixing syringe barrel 1006. The detached plunger seal 1066 is initially located proximal to the bypass channel 1060 and completely separates the dry sealant component 1062 from the liquid sealant component 1064. The dry sealant component 1062 can be, for example, polyethylene glycol (PEG) and the liquid sealant component 1064 can be albumin in water solution. The liquid sealant component 1064 advantageously can comprise additional water to make up for the difference in normal water that is pre-mixed with the dry sealant component A 1062 used in other embodiments. When the syringe plunger coupler 1026 is advanced distally causing the syringe plungers 1028 and the syringe plunger gaskets 1022 to advance distally, the chamber holding the liquid sealant component 1064 becomes pressurized and moves the detached plunger seal 1066 distally so that the bypass channel 1060 is exposed to the liquid sealant component 1064, thus allowing the liquid sealant component 1064 to flow through the bypass channel 1060 and mix with the dry sealant component A 1062. Further distal advance of the plunger coupler 1026 causes the buffering solution 1038 and the mixed components 1062 and 1064 to be propelled through the one-way valves 1044, through the manifold 1030 and into the mixing head 1050, which mixes the components 1062 and 1064 with the buffering solution 1038. The buffering solution 1038 also contains water or other solvent and the amount of water added in the buffering solution 1038 needs to be factored into the total for the resultant sealant compound. The mixed, buffered sealant is ejected into the aerosol head 1016 and is combined with high-pressure gas, which enters through the aerosol pressure fitting 1052 prior to being ejected into space distal to the aerosol head 1016. Alternatively, the plunger coupler 1026 may be omitted, and each of the plungers 1028 and the plunger gaskets 1022 are advanced at different rates so that control over mixing parameters can be maximized. The syringe plunger coupler 1026 can be advanced or retracted using pneumatic force, hydraulic force, electromagnetic force, or manually applied force.

During storage, the dry sealant component 1062 can be pressurized with an inert gas such as nitrogen, argon, helium, or the like, to prevent or delay oxidation and increase shelf life. The pressurization is preferably set at relatively low levels, less than 5 PSI, and is easily overcome by the pressure exerted by distal movement of the plungers 1028. The detached plunger seal 1066 is fabricated from silicone elastomer, polytetrafluoroethylene, fluorinated ethylene propylene, polyurethane, thermoplastic elastomer, or the like. It is configured preferably with external, circumferentially disposed ribs, peaks and valleys, to enhance the seal and can further comprise a central hollow region on its distal aspect to cause radial expansion upon positive pressure being exerted on its distal aspect, for example by the inert gas described earlier in this paragraph. The detached plunger seal 1066 can further be coated with metallic foil, polymer coatings such as silicone, glass, or the like, on the proximal surface, the distal surface or both to minimize material diffusion therethrough. The mixing syringe barrel 1006 can have a smaller inner diameter in the region just proximal to the location of the detached plunger so that pressurization is not able to push the detached plunger proximally against the inward transition zone between the two inner diameters. The syringe plunger gaskets 1022 do not need to have entirely perfect seals and are configured for high levels of radial expansion to maintain the seal even after the plunger 1066 is advanced distally into the larger internal diameter portion of the mixing syringe barrel 1006. The high levels of expansion can be enabled using folded circumferential ribs or very low durometer resilient materials, or both.

The syringe manifold 1030, the one-way check valves 1044, and the mixing chamber 1050 can be coated with materials that have a low pH and are thus, acidic. The acidic surfaces will help prevent gelling of the mixed sealing compound while within the internal lumens of the dispenser 1000. Further measures to prevent clogging of the device 1000 include providing a bolus of gas, water, alcohol, or other substance to flush out the internal volume of the manifold 1030 and the mixing chamber 1050 after forward, or distal, movement of the syringe plungers 1028 has ceased. Such a bolus of materials is preferably automatically dispensed so that the user does not have to perform any conscious cleaning procedures. In the aerosol or pneumatically driven system, sufficient gas can be made available to clean out the lines after the trigger is released. Ball valves or stopcocks can be used instead of the one-way check valves 1044 and those ball valves can be manually operated or motor, pneumatic, hydraulic, or electrical solenoid driven. In some embodiments, the self-purging apparatus disclosed in U.S. Provisional Patent Application No. 61/320,909, filed Apr. 5, 2010 entitled SYSTEMS, DEVICES, METHODS FOR DELIVERING HYDROGEL COMPOSITIONS WITH SELF-PURGING TO PREVENT CLOGGING, hereby incorporated by reference, may also be incorporated into the apparatus.

Figure 11:
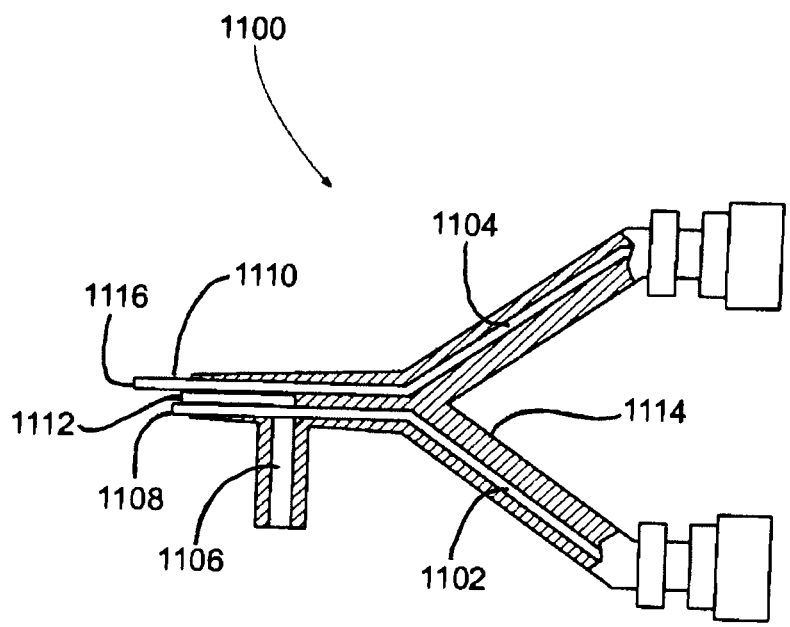
FIG. 11 illustrates a close-up, partially cut-away aerosol tip configuration wherein the protein component channel exit is positioned proximal to the cross-linking component channel exit, according to an embodiment of the invention.

FIG. 11 illustrates an alternate aerosol tip configuration wherein the protein component channel exit is positioned proximal to the cross-linking component channel exit. The aerosol tip configuration 1100 comprises a protein component channel 1102, a cross-linking component channel 1104, an aerosol channel 1106, a protein component channel end 1108, a cross-linking channel end 1110, an aerosol channel end 1112, and a support structure 1114. The protein component channel 1102 can be a metal or polymer axially elongate tube with an outer diameter and an inner diameter, which defines the outer wall of the lumen. The cross-linking component channel 1104 comprises metal or polymeric axially elongate tube with an outer diameter and an inner diameter, which defines the outer wall of the flow lumen. The aerosol channel 1106 comprises metal or polymeric axially elongate tube with an outer diameter and an inner diameter, which defines the outer wall of the flow lumen through which high-pressure gas passes to generate the aerosol effect. The protein component channel 1102 has a distal end or exit 1108, which is positioned proximal relative to the end or exit 1110 of the cross-linking component channel 1104. The area forms a mixing area 1116, similarly to the mixing heads described with respect to the prior drawings and embodiments. As such, the mixing area or mixing head of the present invention should be read broadly to include any area or structure that provides a mixing area that will not allow clogging or clotting of the general delivery device. The relative separation between the two channel ends 1108 and 1110 is between 1 and 10 mm with a preferred range of 2 to 7 mm. With this configuration, the cross-linking component is mixed with the protein in space far from the lumen of the protein component channel 1102 so that the protein component channel 1102 cannot receive any backsplash or backflow of cross-linked protein, which might clog the lumen.

Furthermore, the dilution of the protein, which contacts the cross-linking fluid, reduces the clogging propensity of the gelled compound inside the delivery system. A small volume of protein mixing with a large volume of cross-linking agent results in less propensity to gel than if the same volume of cross-linking agent is mixed with a larger volume of protein. The bolus of protein can be diluted with water to achieve the correct volume ratio. For example, with a ratio of PEG to albumin of 10 to 1, the initial integrity of the compound and its propensity to gel is lower than if the ratio of PEG to albumin is 1 to 10. The flow of cross-linking agent through the channel 1104 will keep this channel clear from clogging or obstruction. The aerosol channel end 1112 is positioned either proximal or distal to the protein component channel end 1108, although it is preferably located proximal to the protein component channel end 1108, as illustrated in FIG. 11. The support structure 1114 is generally polymeric although it can be metal and supports the channels 1102, 1104 and 1106, although it could be polymeric and said channels can be integrally formed with the polymeric support structure 1114 by injection molding, machining, or the like.

Figure 12:
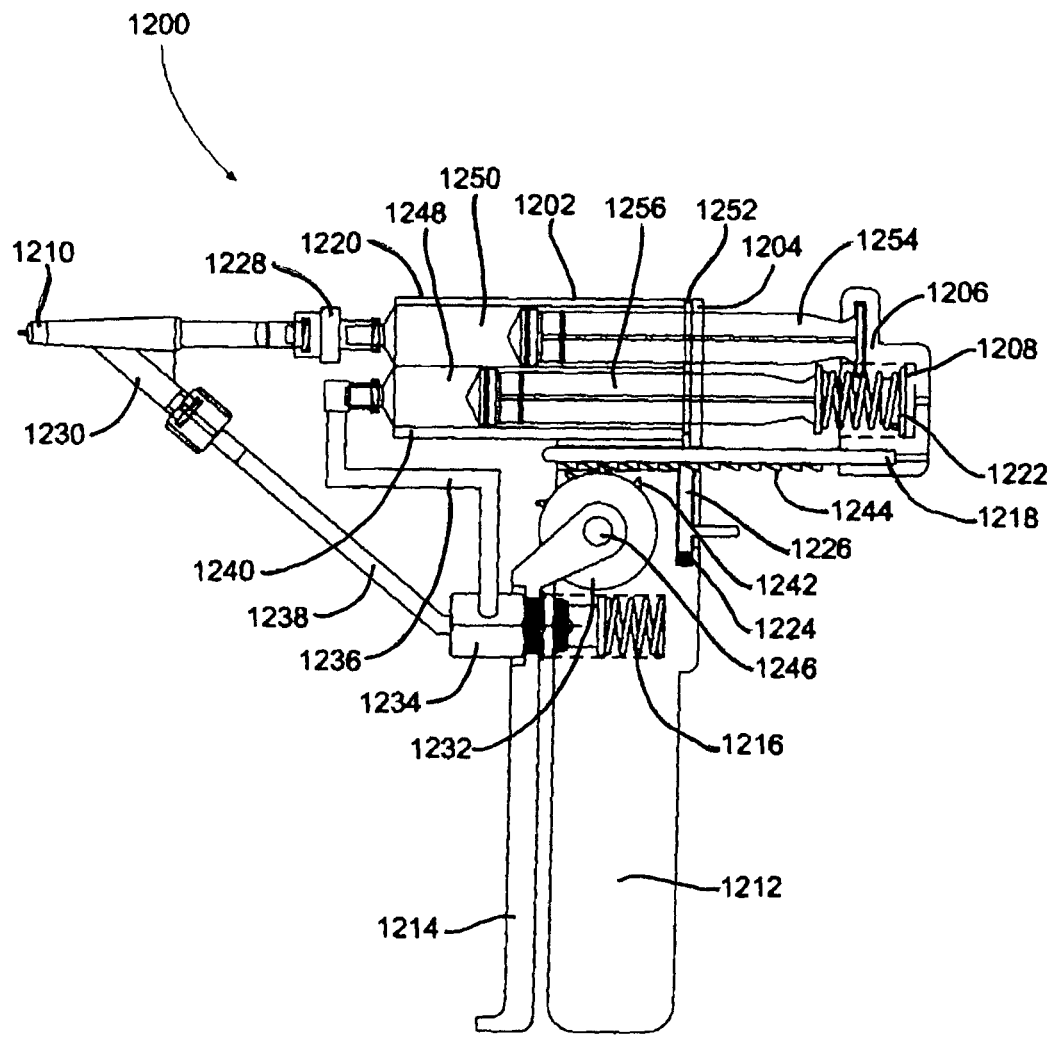
FIG. 12 illustrates a partially cut-away side view of a manually powered applicator wherein the distal channels through which the gel components are delivered are cleared by a bolus of water following each application, according to an embodiment of the invention.

FIG. 12 illustrates a spray applicator 1200 for a multi-component gel, wherein the applicator 1200 comprises line and spray head cleaning means. The spray applicator 1200 comprises a carrier housing 1202, a carrier back plate 1204, a plunger coupler 1206, a spring plate 1208, a spray head 1210, a handle 1212, a trigger 1214, a ratchet lock 1216, a ratchet rod 1218 further comprising a plurality of ratchet rod teeth 1244, a plurality of component syringes 1220, further comprising component syringe plungers 1254, a plunger spring 1222, a lock spring 1224, a valve spring 1226, a plurality of 1-way valves 1228, a manifold 1230, a ratchet wheel 1232 further comprising a plurality of ratchet wheel teeth 1242, a flushing valve 1234, a valve inlet line 1236, a valve outlet line 1238, a flushing syringe 1240, further comprising a flushing syringe plunger 1256, a volume of flushing fluid 1248, a plurality of volumes of gel component 1250, a syringe carrier groove 1252, and an axle 1246.

Referring to FIG. 12, the carrier housing 1202 is a clip that holds the syringes 1220 1240 to the housing 1202, with the handle being affixed, either permanently or removably, to the handle 1212. The carrier housing 1202 surrounds the syringes 1240 and 1220 so as to restrict axial and lateral syringe motion. The carrier back plate 1204 can be integral to the carrier housing 1202 or it can be separate and affixed by bonding, connectors, or the like. In the case where the carrier back plate 1204 is integral to the carrier housing 1202, the syringes 1220 are inserted from the top and the groove 1252 separates the carrier housing 1202 and carrier back plate 1204 such that a flange on the back of each of the syringe barrels 1220 and 1240 is trapped by the groove 1252 and restricted from axial motion. The syringes 1220 and 1240 can be inserted from the top or other lateral direction, so that the flange fits into the groove 1252 or the syringes 1220 and 1240 can be inserted from the back of the carrier housing 1202 and the carrier back plate 1204 attached by connectors such as screws, quick connects, clips, or the like. The plunger coupler 1206 traps flanges on the back of the component syringe plungers 1254 in a groove such that movement of the plunger coupler 1206 in the forward or backward direction causes axial movement of the component syringe plungers 1254. The plunger coupler 1206 is affixed to the ratchet rod 1218. The plunger coupler 1206 is affixed to the spring plate 1208, which further retains the plunger spring 1222 from lateral motion by way of an internal lip (not shown). The plunger spring 1222 rests against and biases the flushing syringe plunger 1256 to move forward.

The trigger 1214 is constrained to rotate about the axle 1246, which is constrained from lateral and axial motion by the handle 1212. The trigger 1214 is affixed to the ratchet wheel 1232 and rotates in a 1:1 ratio with the ratchet wheel 1232. The ratchet wheel 1232 moves the ratchet wheel teeth 1242 against the ratchet rod teeth 1244 to advance the ratchet rod 1218 forward. Reverse motion of the ratchet wheel 1232 causes the ratchet wheel teeth 1242, which are spring loaded to retract, biased by the ramps on the forward side of the ratchet rod teeth 1244 to allow relative reverse motion between the ratchet wheel teeth 1242 and the ratchet rod teeth 1244. The ratchet lock 1216 is slideably affixed within the handle 1212 so as to permit axial motion only, biased upward by the lock spring 1224 so that its sharp upper end engages the ratchet rod teeth 1244. Downward pressure on the ratchet lock 1216 by ramping over the sloped forward edges of the ratchet rod teeth 1244 disengages its upper end from the ratchet rod teeth 1244 and permits the ratchet rod teeth 1244 to move forward. Downward manual pressure on the ratchet lock 1216 disengages the upper end of the ratchet lock 1216 form the ratchet rod teeth 1244 and permits the ratchet rod teeth 1244 and the ratchet rod 1218 to move backward. When the ratchet rod 1218 moves forward, it forces the plunger coupler 1206 to move forward. The plunger coupler 1206 forces the plurality of component syringe plungers 1254 to move forward to expel the plurality of gel components 1250 through the plurality of one way valves 1228 into the manifold 1230 and out the mixing head 1210. Forward motion of the plunger coupler 1206 also compresses the plunger spring 1222, which then exerts increasing force on the flushing syringe plunger 1256 and pressurizes the flushing fluid 1248. In some embodiments, a pressure assist mechanism (not shown) may be employed to ensure an even flow. A spring or gas-assisted mechanism can be employed to even trigger pulls. For example, the spring or gas-assist absorbs heavy pulls, and redistributes the pull energy to evenly dispense material. In light pulls, the spring or gas-assist may simply absorb the pull energy and dissipate it within the system, dispensing only upon appropriate pressure. Other alternative arrangements will be apparent.

In a possible arrangement, the flushing valve 1234 is closed when the trigger 1214 is being pulled toward the handle 1212 so pressurized flushing fluid 1248 cannot flow through the system. The flushing valve 1234 is affixed to the trigger 1214. The valve spring 1226 is affixed at one to the handle 1212 and constrained from lateral motion. The valve spring 1226 presses against the actuator, or button, of the flushing valve 1234 to keep the flushing valve 1234, which is normally open, in the closed position. When the trigger 1214 is withdrawn toward the handle 1212, the valve spring 1216 is compressed and maintains closure of the flushing valve 1234. When the trigger 1214 is released to move away from the handle 1212, the force exerted by the valve spring 1216 is lessened and the normally open flushing valve 1234 opens. The inlet of the flushing valve 1234 is connected to the outlet of the flushing syringe 1240 by the valve inlet line 1236. The outlet of the flushing valve 1234 is connected to the manifold 1230 by the valve outlet line 1238. A part of the volume of flushing fluid 1248, which becomes pressurized by flushing syringe plunger 1256 advancement, flows from the flushing syringe 1240, through the valve inlet line 1236, through the open flushing valve 1234, through the valve outlet line 1238 and into the manifold 1230 and mixing head 1210 to clean out residual gel components (not shown).

In use, the dispenser or applicator 1200 works by preparing the gel components 1250. This may include having to pre-mix powdered materials such as polyethylene glycol and water or buffered water. The mixing head 1210 is aimed at the target tissue. The trigger 1214 is pulled toward the handle 1212. This causes the flushing valve 1234 to close and the plunger coupler 1206 to be pulled forward causing ejection of the gel components 1250 so that they are sprayed onto the target tissue through the mixing head 1210. A solid cone spray pattern of approximately 0.5 to 10 cm diameter at 1 to 20 cm distance is beneficial in these applications. During gel spraying, the flushing valve 1234 is closed so the flushing syringe plunger 1256 cannot move forward even though it is under increasing pressure exerted by the plunger spring 1222 which is increasingly compressed by the plunger coupler 1206. The trigger 1214 is pulled through sufficient distance so that it preferably completely discharges a pre-determined amount of gel component from each syringe 1220. Such pre-determined amount of gel component 1250 can range from 0.1-cc to 5-cc with a preferred range of 0.5 to 2-cc. When the trigger 1214 is released, the ratchet mechanism maintains the position of the plunger coupler 1206 but the flushing valve 1234 is opened, thus allowing the flushing fluid 1248 to flow through the manifold 1230 and the mixing head 1210. The flushing fluid 1248 can be ejected in volumes of 0.1-cc to 10-cc with a preferred range of 0.25 to 1-cc. The flushing fluid can be water, buffered water, saline, or in a pneumatic embodiment, high-pressure air, carbon dioxide, nitrogen, or other gas. The flushing fluid 1248 cleans out the manifold 1230 and the mixing head 1210 to prevent clogging. In another embodiment, the flushing fluid 1248 can be routed into the gel component lines at a point even closer to the one-way valves 1228 to achieve additional flushing. It is, practically, only necessary to flush out those lines where mixed gel components flow. The separate gel components 1250 are preferably not capable of clogging the lines by themselves. The materials used in construction of the flushing applicator 1200 are the same as those used in other applicators disclosed herein. Syringe 1240 and 1220 volumes can range from 0.5-cc to 20-cc with a preferred range of 1-cc to 10-cc. The gel component syringes 1220 can be lyophilizing syringes to permit in-syringe mixing of components following selective breakdown of an internal barrier between multiple syringe contents.

Preferably, the flushing valve 1234 is a two way normally closed valve and the valve spring 1216 is configured only to bias and push the trigger 1214 away from the handle 1212 without contacting or operating the flushing valve 1234 in any way. In this arrangement, the flushing valve 1234 is closed when the trigger is away from the handle 1212 or as the trigger 1214 is pulled toward the handle 1212. The flushing valve 1234 opens only when the trigger 1214 is pushed against the handle 1212 such that the pushbutton on the flushing valve 1234 is depressed by the handle, thus causing flushing valve 1234 opening and flushing fluid 1248 can now flow through the manifold 1230 and spray head 1210. When the trigger 1214 is released the handle 1212 no longer pushes on the button of the flushing valve 1234 and the flushing valve 1234 closes.

Alternatively, the flushing applicator system 1200 can have the flushing valve 1234 affixed to the handle 1212 while the valve spring 1226 is constrained between the one-way valve 1234 button and the trigger 1214. As such, flexible lines are not necessary and the valve inlet and outlet lines 1238 and 1238, respectively can be routed through the handle 1212 and be invisible to the user.

In another arrangement, the flushing system can be achieved using high-pressure gas to clean out the line. The high-pressure gas can be sourced from a canister of pressurized gas contained within the applicator. The flushing system can use position sensors, and electronic controls to determine when to open the flushing valves. Such systems can be powered by on-board batteries and use sensors such as Hall-effect sensors and magnets or LVDT devices to gauge when to execute line flushing. In another embodiment, the flushing system can use a normally open or normally closed valve, which opens or closes to allow the flow of purging gas (depending on the type of valve and flow channel configuration) when compressed against the trigger 1214 and the handle 1212. It is beneficial not to flush the lines when the gel is being discharged.

The present invention may be embodied in other specific forms without departing from its spirit or essential characteristics. For example, the material used to seal the vessel defect can comprise human albumin and polyethylene glycol solution, or it may comprise a multi-part mixture of non-human or recombinant albumin and polyethylene glycol. Additional chemicals may be injected along with, or prior to, the sealing components in order to cause a beneficial change in the polymerization characteristics, adhesive characteristics, or lubricity of the resultant sealing matrix. The sealing compound may be resorbable or non-resorbable in the body. Further, the sealing compound may have its lubricity and adhesive characteristics altered, for instance by changing the pH of the environment. The dispenser can be used for thoracoscopic use as well as laparoscopic use. Multiple or combination power systems can be used to enable device function. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A portable pneumatic aerosol device for delivering a multi-component sealing compound, the device comprising:
   a housing;
   at least two independent component containing reservoirs, wherein each independent component containing reservoir includes a moveable plunger;
   a pneumatic device including a pneumatic cylinder and a movable rod that is operatively coupled to each plunger;
   a mixing head having a plurality of inlets and an outlet, each of the inlets connected to one of the reservoirs, the mixing head providing a mixing area for the at least two independent components to form the multi-component sealing compound;
   an aerosol pressure regulator fluidly connected to the mixing head;
   a pneumatic pressure regulator fluidly connected to the pneumatic device and the aerosol pressure regulator; and
   a pressurized gas cartridge fluidly connected to the mixing head through the aerosol pressure regulator, the pressurized gas cartridge fluidly connected to the pneumatic device through the aerosol pressure regulator and the pneumatic pressure regulator, wherein the pressurized gas cartridge is selectively actuable to pressurize the pneumatic device to drive the movable rod of the pneumatic cylinder to move each operatively coupled plunger in the at least two independent component containing reservoirs to force the independent components from the at least two independent component containing reservoirs through the plurality of inlets and into the mixing head, and wherein the pressurized gas cartridge is selectively actuable to force gas directly into the mixing head upstream of the mixing area to force the multi-component sealing compound through the mixing head outlet,
   wherein each of the reservoirs, the aerosol pressure regulator, the pneumatic pressure regulator, and the pressurized gas cartridge is at least partially located within the housing.

2. The device of claim 1, wherein the reservoirs are releasably attached to the housing.

3. The device of claim 1, wherein the aerosol pressure regulator is adjustable to change a pressure of gas forced into the mixing head.

4. The device of claim 3, wherein the pressurized gas cartridge fluidly connected to the pneumatic device through the aerosol pressure regulator and the pneumatic pressure regulator and the pneumatic pressure regulator is adjustable to change a pressure of gas forced into the pneumatic cylinder.

5. The device of claim 4, wherein the pressure of gas forced into the mixing head is different than the pressure of gas forced into the pneumatic cylinder.

6. The device of claim 1, wherein the aerosol pressure regulator reduces a pressure of gas supplied from the pressurized gas cartridge to a pressure of gas forced into the mixing head in the range of 10-20 PSI.

7. The device of claim 1, wherein the pneumatic pressure regulator reduces a pressure of gas supplied from the pressurized gas cartridge to a pressure of gas forced into the pneumatic cylinder in the range of 10-20 PSI.

8. The device of claim 1, wherein the device is free from any connections to external power supplies or gas supplies.

9. The device of claim 1, further comprising:
   a trigger configured to selectively actuate the pressurized gas cartridge; and
   a first lock affixed to the housing and configured to selectively engage a first moveable plunger of the at least two independent component containing reservoirs to prevent movement of the first moveable plunger.

10. The device of claim 9, further comprising a second lock affixed to the housing and configured to selectively engage a second moveable plunger of the at least two independent component containing reservoirs to prevent movement of the second moveable plunger.

11. The device of claim 9, wherein the first lock is configured to engage a lock notch formed in the first moveable plunger.

12. The device of claim 1, further comprising:
   a power source; and
   an electric pneumatic pump disposed in the housing and fluidly connected to the pressurized gas cartridge, wherein the electric pneumatic pump is configured to pressurize the pressurized gas cartridge, and wherein the electric pneumatic pump is selectively powered by the power source.

13. The device of claim 12, wherein the power source is a battery, wherein the battery is configured to removably attach to the housing.

14. The device of claim 1, wherein the housing comprises a main housing and a syringe head, wherein the aerosol pressure regulator, the pneumatic pressure regulator, and the pressurized gas cartridge are at least partially located within the main housing, and wherein the at least two independent component containing reservoirs are at least partially located within the syringe head, and wherein the main housing includes an attachment prong configured to be received in an attachment slot of the syringe head to releasably secure the syringe head to the main housing.

15. The device of claim 1, wherein a first component containing reservoir of the at least two independent component containing reservoirs includes a separator plunger configured to divide the independent component containing reservoir into two compartments, and wherein the first component containing reservoir includes a bypass channel configured to selectively fluidly connect the two compartments.

16. The device of claim 1, wherein the at least two independent component containing reservoirs are three independent component containing reservoirs.

17. A portable pneumatic aerosol device for delivering a multi-component sealing compound, the device comprising:
- a housing;
- a first component containing reservoir including a first moveable plunger;
- a second component containing reservoir including a second moveable plunger;
- a third component containing reservoir including a third moveable plunger;
- a pneumatic device including a pneumatic cylinder and a movable rod that is operatively coupled to the first moveable plunger;
- a mixing manifold fluidly connecting the first component containing reservoir to the second component containing reservoir, wherein the mixing manifold provides a first mixing area for the first component and the second component to form a first mixture;
- a mixing head having a first inlet, a second inlet, and a mixing head outlet, wherein the first inlet is fluidly connected to the mixing manifold, wherein the second inlet is connected to the third component containing reservoir, the mixing head providing a second mixing area for the first mixture and the third component to form the multi-component sealing compound; and
- a pressurized gas cartridge fluidly connected to the mixing head and the pneumatic device, wherein the pressurized gas cartridge is selectively actuable to pressurize the pneumatic device to drive the movable rod of the pneumatic cylinder to move the first moveable plunger in the first component containing reservoir and the third moveable plunger in the third component containing reservoir to force the first mixture and the third component through the first inlet and second inlet and into the mixing head, and wherein the pressurized gas cartridge is selectively actuable to force gas directly into the mixing head upstream of the second mixing area to force the multi-component sealing compound through the mixing head outlet.

18. The device of claim 17, further comprising:

an aerosol pressure regulator fluidly connected to the mixing head; and a pneumatic pressure regulator fluidly connected to the pneumatic device, wherein the first component containing reservoir, the second component containing reservoir, the third component containing reservoir, the aerosol pressure regulator, the pneumatic pressure regulator, and the pressurized gas cartridge are at least partially located within the housing.

* * * * *